(12) United States Patent
Feghali-Bostwick et al.

(10) Patent No.: US 8,969,326 B2
(45) Date of Patent: Mar. 3, 2015

(54) ESTROGEN ANTAGONISTS AS TREATMENTS FOR SCLEROSING DISORDERS

(75) Inventors: Carol A. Feghali-Bostwick, Pittsburgh, PA (US); Pamela Anne Hershberger, Clarence Center, NY (US)

(73) Assignee: University of Pittsburgh—Of The Commonwealth System Of Higher Education, Pittsburgh, PA (US)

( * ) Notice: Subject to any disclaimer, the term of this patent is extended or adjusted under 35 U.S.C. 154(b) by 94 days.

(21) Appl. No.: 13/352,602

(22) Filed: Jan. 18, 2012

(65) Prior Publication Data

US 2012/0135971 A1 May 31, 2012

Related U.S. Application Data

(63) Continuation of application No. PCT/US2010/043418, filed on Jul. 27, 2010.

(60) Provisional application No. 61/231,899, filed on Aug. 6, 2009, provisional application No. 61/271,965, filed on Jul. 28, 2009.

(51) Int. Cl.
| | |
|---|---|
| *A61K 31/565* | (2006.01) |
| *A61K 31/453* | (2006.01) |
| *A61K 31/138* | (2006.01) |
| *A61K 31/4453* | (2006.01) |
| *A61K 31/085* | (2006.01) |
| *A61K 31/216* | (2006.01) |
| *A61K 31/4535* | (2006.01) |

(52) U.S. Cl.
CPC ............ *A61K 31/138* (2013.01); *A61K 31/565* (2013.01); *A61K 31/4535* (2013.01)
USPC ........... 514/171; 514/182; 514/320; 514/648; 514/319; 514/720

(58) Field of Classification Search
None
See application file for complete search history.

(56) References Cited

U.S. PATENT DOCUMENTS

| | | | |
|---|---|---|---|
| 6,794,403 | B2 | 9/2004 | Malamas et al. |
| 7,279,499 | B2 | 10/2007 | Durst et al. |
| 7,442,812 | B2 | 10/2008 | Durst et al. |
| 2002/0049198 | A1 | 4/2002 | Littman |
| 2002/0077317 | A1 | 6/2002 | Das |

FOREIGN PATENT DOCUMENTS

| | | |
|---|---|---|
| EP | 1 448 206 | 8/2004 |
| WO | WO 2004/062653 | 7/2004 |
| WO | WO 2006/004451 | 4/2006 |
| WO | WO 2008/009927 | 1/2008 |

OTHER PUBLICATIONS

Thomas-Golbanov et al. in Clinical and Experimental Rheumatology 2003;21:99-102.*
Gartner et l. in Journal of Mass Spectrometry 2008; 43: 958-964.*
Gibson et al. in British Journal of Rheumatology 22(4):218-223 (1983).*
Wigley et al. in Expert Opinion on Investigational Drugs 10(1): 31-48, 2001.*
Sapadin et al. in Archives of Dermatology, 138, 99-105 (2002).*
International Search Report for PCT/US2010/043418, dated Oct. 8, 2010.
Bentrem, et al. Molecular Mechanism of Action at Estrogen Receptor α of a New Clinacally Relevant Antiestrogen (GW7604) Related to Tamoxifen, Endocrinology, 142 838-846 (2001).
Ashcroft, et al., "Topical Estrogen Accelerates Cutaneous wound Healing in Aged Humans Associated with an Altered Inflammatory Response", *Am. J. Pathol.*, 155(4):1137-1146 (1999).
Ashcroft, et al., "Estrogen Accelerates Cutaneous Wound Healing Associated with an Increase in TGF-β1 Levels", *Nat. Med.*, 3(11):1209-1215 (1997).
Bakos, et al., "Ultrasonographical and Hormonal Description of the Normal Ovulatory Menstrual Cycle", *Acta Obstet Gynecol Scand.*, 73(10):790-796 (1994).
Beretta, et al., "Hormone Replacement Therapy May Prevent the Development of Isolated Pulmonary Hypertension in Patients with systemic Sclerosis and Limited Cutaneous Involvement", *Scand. J. Rheumatol.*, 35(6):468-471 (2006).
Blizzard, et al., "Estrogen Receptor Ligands. Part 13: Dihydrobenzoxathiin SERAMs with an Optimized Antagonist Side Chain", *Bioorg Med chem.*, 15(17):3912-3916 (2005).
Bowers, et al., "Resveratrol Acts as a Mixed Agonist/Antagonist for Estrogen Receptors α and β", *Endocrinology*, 141(10):3657-3667 (2000).
Brincat, et al., "Long-Term Effects of the Menopause and Sex Hormones on Skin Thickness", *Br. J. Obstet Gynaecol.*, 92(3):256-259 (1985).
Callens, et al., "Does Hormonal Skin Aging Exist? A Study of the Influence of different Hormone Therapy Regimens on the Skin of Postmenopausal Women using Non-Invasive Measurement Techniques", *Dermatology*, 193(4):289-294 (1996).
Campbell-Thompson, et al., "Expression of Estrogen Receptor (ER) Subtypes and ERβ Isoforms in Colon Cancer", *Cancer Research*, 61(2):632-640 (2001).
Chang, et al., "Mammalian MAP Kinase Signalling Cascades", *Nature*, 410(6824):37-40 (2001).
Curran, et al., "Fulvestrant", *Drugs*, 61(6):807-813 (2001).
Cvoro, et al., "Selective Estrogen Receptor-β Agonists Repress Transcription of Proinflammatory Genes", *J. Immunol.*, 180(1):630-636 (2008).
Deroo, et al., "Estrogen Receptors and Human Disease", *The Journal of Clinical Investigation*, 116(3):561-570 (2006).
Diel, et al., "In Vivo Test Systems for the Quantitative and Qualitative Analysis of the Biological Activity of Phytoestrogens", *J. Chromatogr B. Analyt. Technol. Biomed Life Sci.*, 777(1-2):191-202 (2002).

(Continued)

*Primary Examiner* — Dennis Heyer
(74) *Attorney, Agent, or Firm* — Baker Botts L.L.P.

(57) ABSTRACT

The present invention relates to methods and compositions for treating a subject suffering from a sclerosing disorder, comprising administering, to the subject, an effective amount of an estrogen receptor antagonist ("ERANT"), wherein said ERANT has essentially no estrogen receptor agonist activity under physiologic conditions.

3 Claims, 18 Drawing Sheets

(56) References Cited

OTHER PUBLICATIONS

Figure 1:
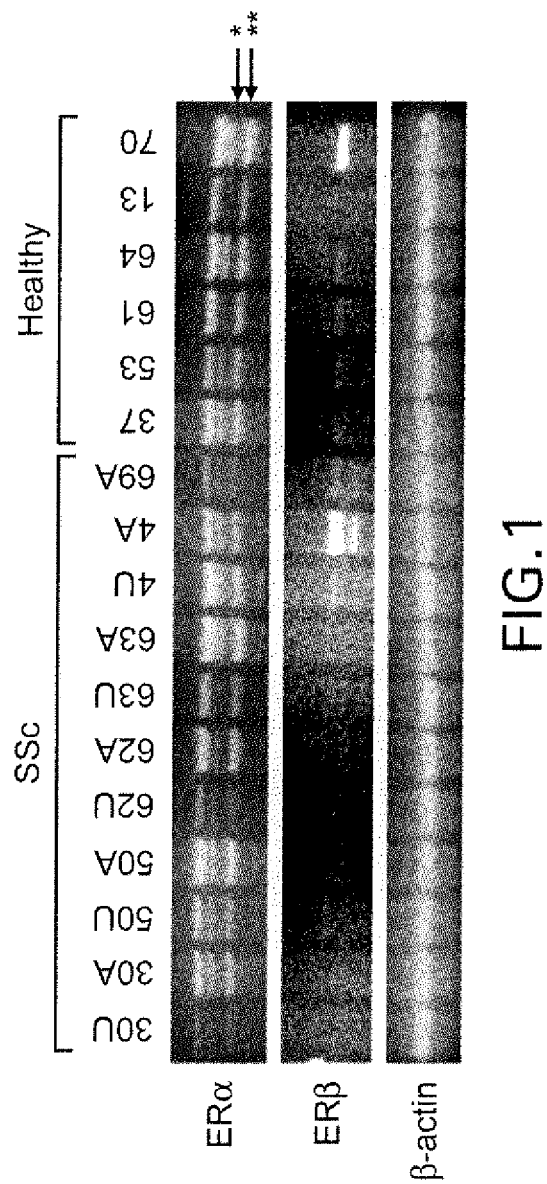

Fan, et al., "Characterization of Molecular and Structural determinants of selective Estrogen Receptor Downregulators", *Breast Cancer Res. Treat.*, 103(1):37-44 (2007).

Feghali, et al., "Identification of Multiple, Differentially Expressed Messenger RNAs in dermal Fibroblasts from Patients with systemic Sclerosis", *Arthritis Rheum.*, 42(7):1451-1457 (1999).

Feghali-Bostwick, et al., "Analysis of Systemic Sclerosis in Twins Reveals Low Concordance for disease and High Concordance for the Presence of Antinuclear Antibodies", *Arthritis & Rheumatism*, 48(7):1956-1963 (2003).

Foley, et al., "Selective Loss of Estrogen Receptor β in Malignant Human Colon", *Cancer Research*, 60(2):245-248 (2000).

Galcheva-Gargova, et al., "An Osmosensing Signal Transduction Pathway in Mammalian Cells", *Science*, 265(5173):806-808 (1994).

Geiser, et al., "A New Selective Estrogen Receptor Modulator with Potent uterine Antagonist Activity, agonist Activity in Bone, and Minimal Ovarian Stimulation", *Endocrinology*, 146(10):4524-4535 (2005).

Gottlicher, et al., "Transcriptional Cross-Talk, the Second Mode of Steroid Hormone Receptor Action", *J. Mol. Med (Berl.)*, 76(7):480-489 (1998).

Haczynski, et al., "Human Cultures Skin Fibroblasts Express Estrogen Receptor α and β", *Int. J. of Molecular Medicine*, 10(2):149-153 (2002).

Hall, et al., "Estrogen and Skin: The Effects of Estrogen, Menopause, and Hormone Replacement Therapy on the Skin", *J. Am. Acad. Dermatol.*, 53(4):555-568 (2005).

Harris, et al., "A Selective Estrogen Receptor-β Agonist causes Lesion Regression in an Experimentally Induced Model of Endometriosis", *Hum. Reprod.*, 20(4):936-941 (2005).

Harris, et al., "Evaluation of an Estrogen Receptor-β Agonist in Animal Models of Human disease", *Endocrinology*, 144(10):4241-4249 (2003).

Henderson, et al., "Hormonal Carcinogenesis", *Carcinogenesis*, 21(3):427-433 (2000).

Highland, et al., "New Developments in Scleroderma Interstitial Lung Disease", *Current Opinion in Rheumatology*, 17(6):737-745 (2005).

Horvath, et al., "Frequent Loss of Estrogen Receptor-β Expression in Prostate Cancer", *Cancer Research*, 61(14):5331-5335 (2001).

Hurn, et al., "Sex, Steroids, and Stroke", *Stroke*, 35:2642-2643 (2004).

Jassam, et al., "Loss of Expression of Oestrogen Receptor β in Colon Cancer and Its Association with Dukes' Staging", *Oncology Reports*, 14(1):17-21 (2005).

Kim, et al., "Estrogen Signaling in the Cardiovascular System", *Nuclear Receptor Signaling*, 4:e013 (5 pages) (2006).

Konstantinopoulos, et al., "Oestrogen Receptor β (ERβ) is Abundantly Expressed in Normal Colonic Mucosa, but declines in Colon Adenocarcinoma Paralleling the Tumour's Dedifferentiation", *Eur. J. Cancer*, 39(9):1251-1258 (2003).

Leav, et al,, "Comparative Studies of the Estrogen Receptors β and α and the androgen Receptor in Normal Human Prostate Glands, Dysplasia, and in Primary and Metastatic Carcinoma", *The American Journal of Pathology*, 159(1):79-92 (2001).

Levin, "Cellular Functions of Plasma Membrane Estrogen Receptors", *Steroids*, 67(6):471-475 (2002).

Liu, et al., "A Homogeneous In Vitro Functional Assay for estrogen Receptors: Coactivator Recruitment", *Mol. Endocrinol.*, 17(3):346-355 (2003).

Lloyd, et al., "Recent Advances in Estrogen Receptor Antagonists", *Drugs*, 3(6):632-642 (2000).

Maheux, et al., "A Randomized, Double-Blind, Placebo-Controlled Study on the Effect of Conjugated Estrogens on Skin Thickness", *Am. J. Obstet. Gynecol.*, 170(2):642-649 (1994).

Mao, et al., "A New Small Molecule Inhibitor of Estrogen Receptor α binding to estrogen Response elements Blocks Estrogen-Dependent Growth of Cancer Cells", *J. Biol. Chem.*, 283(19):12819-12830 (2008).

Melamed, et al., "Molecular and Kinetic Basis for the Mixed Agonist/Antagonist Activity of Estriol", *Mol. Endocrinol.*, 11(12):1868-1878 (1997).

Mercier, et al., "Ovarian Hormones Induced TGF-β(3) and Fibronectin mRNA but Exhibit a Disparate Action on Cardiac Fibroblast Proliferation", *Cardiovasc. Res.*, 53(3):728-739 (2002).

Meyringer, et al., "Analysis of Gene Expression Patterns in systemic Sclerosis Fibroblasts Using RNA Arbitrarily Primed-Polymerase Chain reaction for differential Display", *J. Rheumatol.*, 34(4):747-753 (2007).

Nilsson, et al., "Mechanisms of Estrogen Action", *Physiological Reviews*, 81(4):1535-1565 (2001).

Notelovitz, et al., "Estradiol Absorption from Vaginal Tablets in Postmenopausal Women", *Obstet, Gynecol.*, 99(4):556-562 (2002).

Odum, et al., "The rodent Uterotrophic Assay: Critical Protocol Features, Studies with Nonyl Phenols, and comparison with A yeast Estrogenicity Assay", *Regul. Toxicol Pharmacol.*, 25(2):176-188 (1997).

Ohlsson, et al., "Obesity and Disturbed Lipoprotein Profile in Estrogen Receptor-α-Deficient Male Mice", *Biochem. Biophys. Res. Commun.*, 278(3):640-645 (2000).

O'Lone, et al., "Genomic Targets of Nuclear Estrogen Receptors", *Mol. Endocrinol.*, 18(8):1859-1875 (20040.

Olson, et al., "p38 MAP Kinase: A Convergence Point in Cancer Therapy", *Trends Mol. Med.*, 10(3):125-129 (2004).

Pilewski, et al., "Insulin-Like Growth Factor Binding Proteins 3 and 5 are Overexpressed in Idiopathic Pulmonary Fibrosis and Contribute to Extracellular Matrix Deposition", *Am J. Pathol.*, 166(2):399-407 (2005).

Razandi, et al., "Plasma Membrane Estrogen Receptors Exist and Functions as Dimers", *Molecular Endocrinology*, 18(12):2854-2865 (2004).

Redaelli, et al., "Synthesis and Biological Activity of Akt/PI3K Inhibitors", *Mini Rev. Med. Chem.*, 6(10:1127-1136 (2006).

Rich, et al., "Resolving Estrogen Receptor agonist/Antagonist Kinetics using Biacore's SPR Technology", *Biacore Journal*, 2:4-6 (2002).

Schrepfer, et al., "The Selective Estrogen Receptor-β Agonist Biochanin A Shows Vasculoprotective Effects without Uterotrophic Activity", *Menopause*, 13(3):489-499 (2006).

Silver, et al., "Systemic Sclerosis and Scleroderma variants", *Arthritis and Allied Conditions; 15th Edition 2005 Lippincott Williams & Wilkins Baltimore*, pp. 1633-1680 (2005).

Soldano, et al., "Effects of estrogens on extracellular Matrix synthesis in cultures of Human Normal and Scleroderma Skin Fibroblasts", *Ann. NY Acad. Sci.*, 1193:25-29 (2010).

Sun, et al., "Antagonists Selective for Estrogen Receptor α", *Endocrinology*, 143(3):941-947 (2002).

Tremblay, et al., "EM-800, A Novel Antiestrogen, Acts as a Pure Antagonist of the Transcriptional Functions of Estrogen Receptors α and β", *Endocrinology*, 139(1):111-118 (1998).

Weihua, et al., "A Role for Estrogen Receptor β in the Regulation of Growth of the Ventral Prostate", *PNAS*, 98(11):6330-6335 (2001).

Wise, et al., "Minireview: Neuroprotective Effects of Estrogen—New Insights Into Mechanisms of Action", *Endocrinology*, 142(3):969-973 (2001).

Xia, et al., "Opposing Effects of ERK and JNK-p38 MAP Kinases on Apoptosis", *Science*, 270(5240):1326-1331 (1995).

Yasuoka, et al., "human skin culture as an Ex Vivo Model for Assessing the Fibrotic Effects of Insulin-Like Growth Factor Binding Proteins",*The Open Rheumatology Journal*, 2:17-22 (2008).

Zhou, et al., "Monozygotic Twins Clinically Discordant for Scleroderma Show Concordance for Fibroblast Gene Expression Profiles", *Arthritis & Rheumatism*, 52(10):3305-3314 (2005).

Ziegler, et al., "Regional hemodynamic Adaptation During the Menstrual Cycle", *Obstet. Gynecol.*, 94(5 Pt 1):695-699 (1999).

Zwart, et al., "Classification of Anti-estrogens According to Intramolecular FRET Effects on Phosphomutants of estrogen Receptor α", *Molecular Cancer Therapeutics*, 6(5):1526-1533 (2007).

* cited by examiner

*p<0.05 by Mann-Whitney U-test

*p<0.05 by Mann-Whitney U-test

ESTROGEN ANTAGONISTS AS TREATMENTS FOR SCLEROSING DISORDERS

PRIORITY CLAIM

This application is a continuation of International Patent Application No. PCT/US2010/043418, filed Jul. 27, 2010, which claims priority to U.S. Provisional Patent Application Ser. No. 61/231,899, filed Aug. 6, 2009, and U.S. Provisional Patent Application Ser. No. 61/271,965, filed Jul. 28, 2009, the contents of both of which are hereby incorporated herein by reference in their entireties.

1. INTRODUCTION

The present invention relates to methods and compositions for treating a subject suffering from a sclerosing disorder, comprising administering, to the subject, an effective amount of an estrogen receptor antagonist ("ERANT").

2. BACKGROUND OF THE INVENTION

Systemic sclerosis ("SSc") is a connective tissue disease characterized by excessive fibrosis of the skin and internal organs due to fibroblast proliferation and excessive production of extracellular matrix ("ECM") (1). The mechanism(s) resulting in fibrosis in SSc are still under investigation. It has been reported that fibronectin ("FN") mRNA levels in SSc dermal fibroblasts are up to ten-fold greater than those in healthy donors (26, 31). Thus FN, a key component of ECM, is abnormally expressed in SSc. There are currently no effective treatments to prevent or halt the progression of fibrosis in SSc and other fibrosing diseases (2).

SSc has a worldwide distribution and is more frequent in women than men (3). The female:male ratio is approximately 3:1. Surprisingly, the ratio increases to 10:1 during the child-bearing years (1). This suggests that female sex hormones such as estrogens and progesterone may contribute to disease pathogenesis.

Estrogens, especially estradiol ("E2"), play an important role in many physiological processes in mammals, including but not limited to reproduction, cardiovascular health, bone integrity, cognition and behavior (3). Given this widespread role for E2 in human physiology, E2 is also implicated in the development or progression of numerous diseases, including various types of cancer (breast, ovarian, colorectal, prostate, endometrial), osteoporosis, neurodegenerative diseases, cardiovascular disease, insulin resistance, endometriosis, and obesity (36, 37, 38, 39, 40). In many of these diseases, estrogen mediates its effects through estrogen receptors ("ERs"), which serve as the targets for many therapeutic interventions.

The clinical effects of hormone replacement therapy ("HRT") and tamoxifen, a selective estrogen receptor modulator ("SERM") have been evaluated in SSc patients (24, 25). HRT was suggested to exert protective effects against the development of isolated pulmonary hypertension in patients with SSc and limited cutaneous involvement (24). Tamoxifen, largely used as an estrogen receptor inhibitor but which has conditional agonist activity, did not improve SSc symptoms (25). Cyclofenil, another SERM which has found use as an anabolic steroid by body builders, has also been explored as a potential treatment for SSc with disappointing results (57).

3. SUMMARY OF THE INVENTION

The present invention relates to methods and compositions for treating a subject suffering from a sclerosing disorder, comprising administering, to the subject, an effective amount of an estrogen receptor antagonist ("ERANT"). In preferred, non-limiting embodiments of the invention, said ERANT has little or essentially no estrogen receptor agonist activity under physiologic conditions. The present invention is based, at least in part, on the discoveries that (i) E2 upregulates FN production via the estrogen receptor α ("ERα") and requires activation of PI3K and p38 MAPK signaling; and (ii) E2 also induces fibrosis in human skin, and its effects are blocked by the ERANT fulvestrant (a.k.a. Faslodex®, ICI 182,780).

In alternative, non-limiting embodiments, the present invention provides for a method for treating a subject suffering from a sclerosing disorder comprising administering, to the subject, an effective amount of an estrogen receptor beta agonist ("ERAG-β") together with an ERANT.

4. BRIEF DESCRIPTION OF THE FIGURES

FIG. 1. RT-PCR analysis of ERα and estrogen receptor beta ("ERβ") mRNA in primary skin fibroblasts from twins discordant for SSc. U, unaffected SSc skin fibroblasts; A, affected SSc skin fibroblasts., indicate splice variants.

Figure 2A:
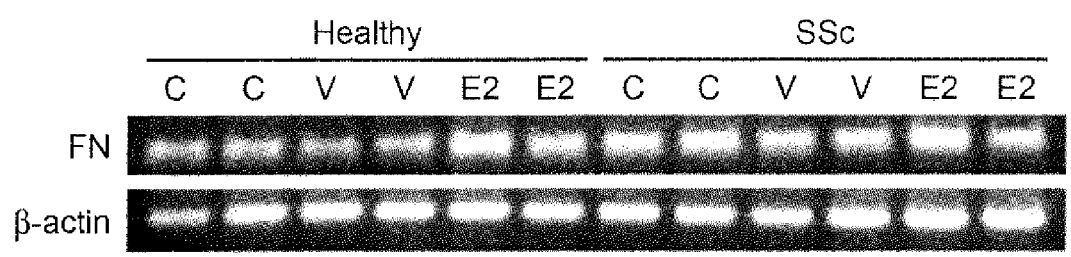
Figure 2B:
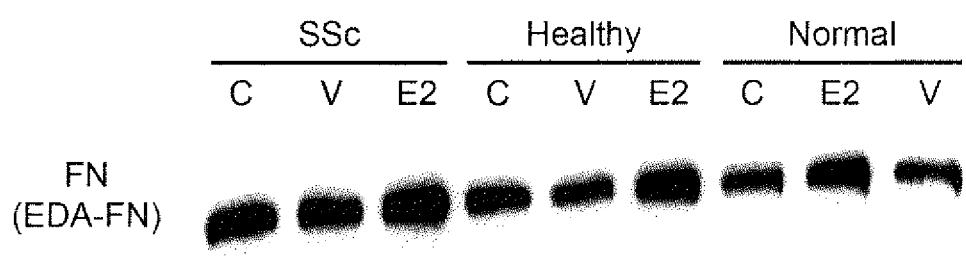

FIG. 2A-B. A. FN mRNA expression in primary skin fibroblasts from twins discordant for SSc. FN mRNA was analyzed after 24-hour treatment with E2, vehicle, or no treatment (control) using RT-PCR. 71: healthy twin, 72: SSc affected twin. B. FN protein expression in culture supernatants of primary skin fibroblasts. FN protein expression was analyzed by western blot in untreated, E2 or vehicle treated fibroblasts for 48 hrs. 71: healthy twin, 72: affected twin, NS: unrelated healthy donor. Molecular weight of EDA-FN; 220 kDa.

Figure 3A:
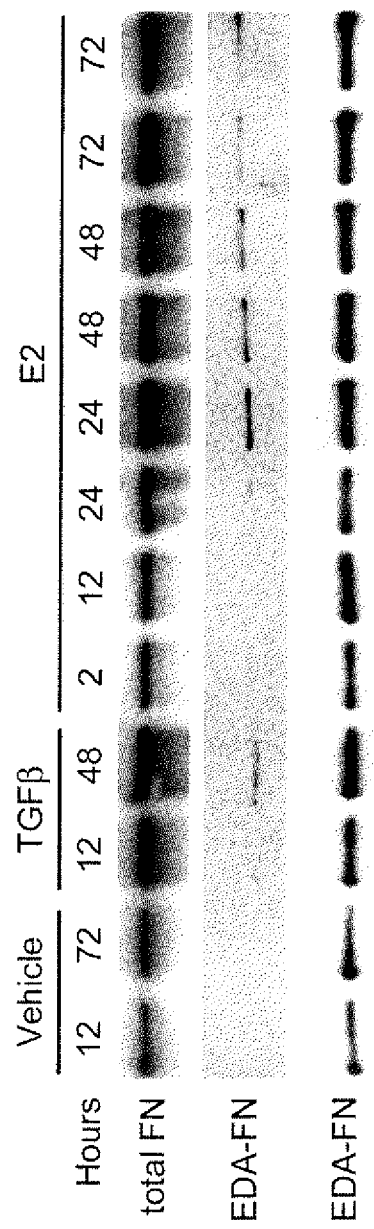
Figure 3B:
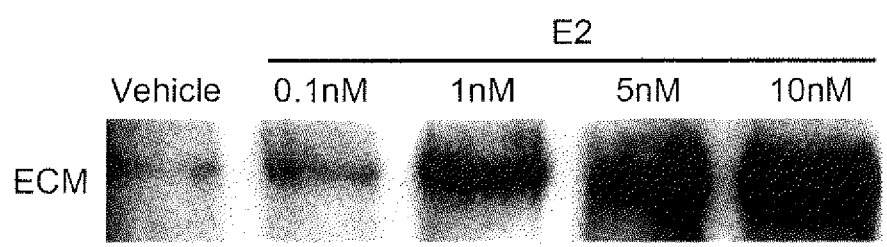

FIG. 3A-B. A. FN protein expression in the extracellular matrix (ECM) and culture supernatants (Sup) of normal skin fibroblasts treated with TGFβ, E2, or vehicle. ECM and culture supernatants were harvested at the indicated time points. B. FN levels in the extracellular matrix (ECM) and culture supernatants (Sup) of normal skin fibroblasts stimulated with vehicle and different concentrations of E2.

Figure 4:
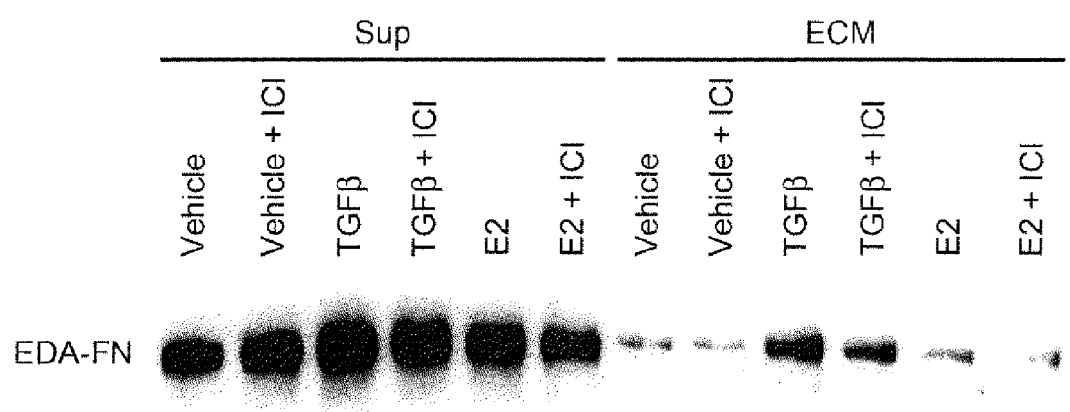

FIG. 4. Effect of E2 blockade on the expression of EN protein in the extracellular matrix (ECM) and supernatants (Sup) of normal skin fibroblasts stimulated with E2. Cells were treated with E2 for 48 hrs in the presence or absence of the E2 antagonist ICI. ICI; ICI 182,780.

Figure 5:
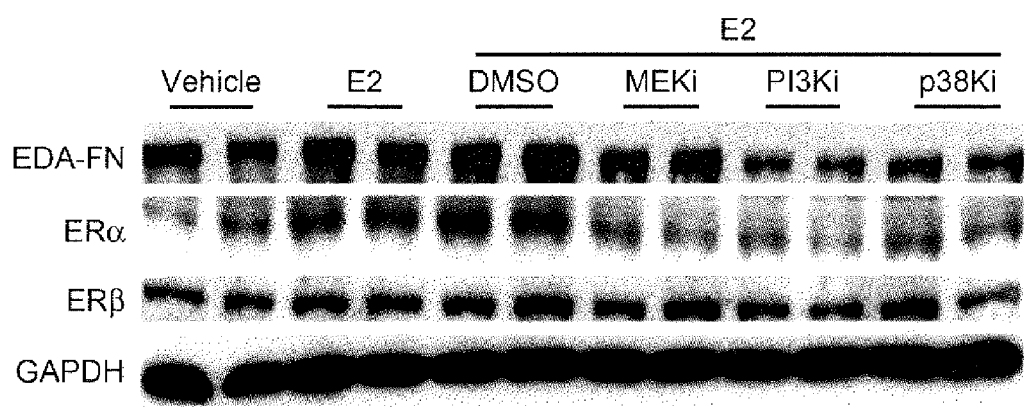

FIG. 5. FN protein levels in the cellular lysates of normal skin fibroblasts. Normal skin fibroblasts were stimulated with E2 for 48 hrs in the presence or absence of the following chemical inhibitors: MEKi; MEK inhibitor, PI3Ki; phosphoinositol 3-kinase inhibitor, p38Ki; p38 kinase inhibitor. Cellular lysates were analyzed by western blot using anti-EDA-FN, ERα, ERβ and GAPDH antibodies.

Figure 6:
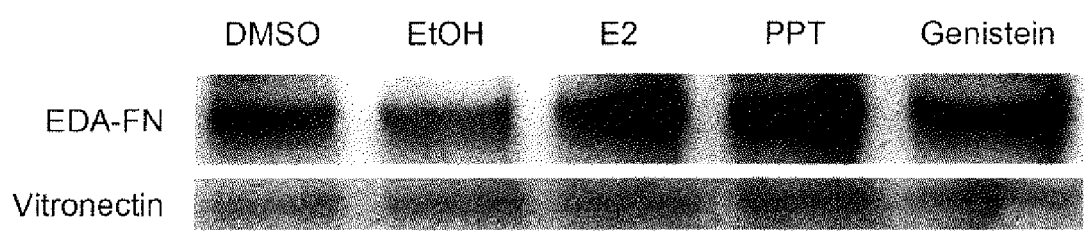

FIG. 6. Effect of E2 ligands on the expression and deposition of FN in the extracellular matrix (ECM) of normal skin fibroblasts. PPT; propyl-pyrazole-triol. Primary fibroblasts were cultured with vehicle (DMSO, Etoh), E2, PPT, or genistein for 48 hrs. ECM was analyzed by western blot using anti-EDA_FN and anti-vitronectin antibodies.

Figure 7A:
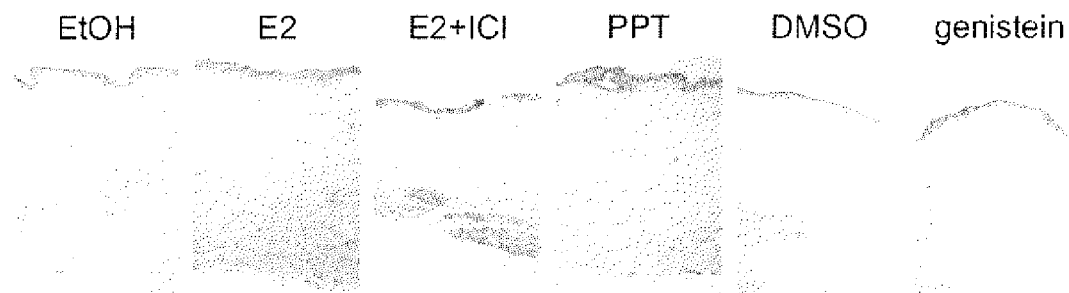
Figure 7B:
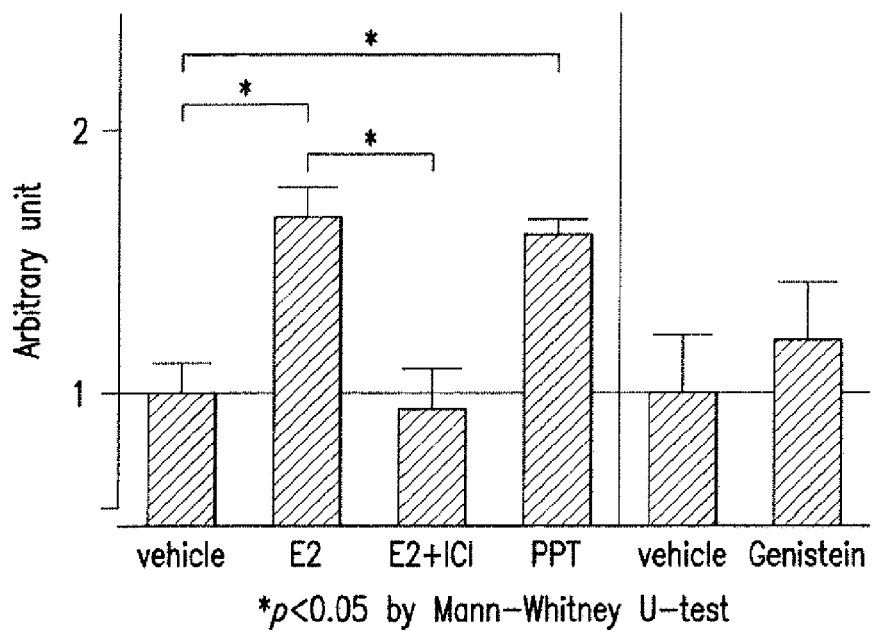

FIG. 7A-B. Estrogen and ER alpha agonist induce skin thickening ex vivo. Human skin samples were plated on to 6-well plate and treated with ethanol (EtOH), Estradiol (E2), estradiol with ICI (E2+ICI), PPT, DMSO, and genistein for 7 days. A. Hematoxylin and Eosin staining of explanted skin. Images were taken at 40× magnification. B. Summary of skin thickness. Skin thickness was measured and the ratio of the thickness compared with vehicle control (EtOH or DMSO) was calculated as an arbitrary unit. Summary of 3 experiments are shown. *p>0.05 by Mann-Whitney U-test.

Figure 8A:
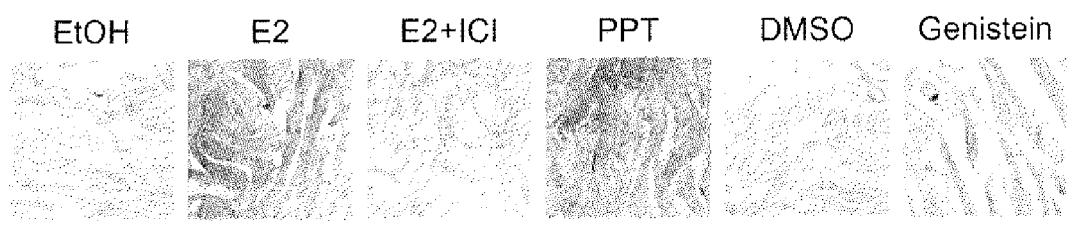
Figure 8B:
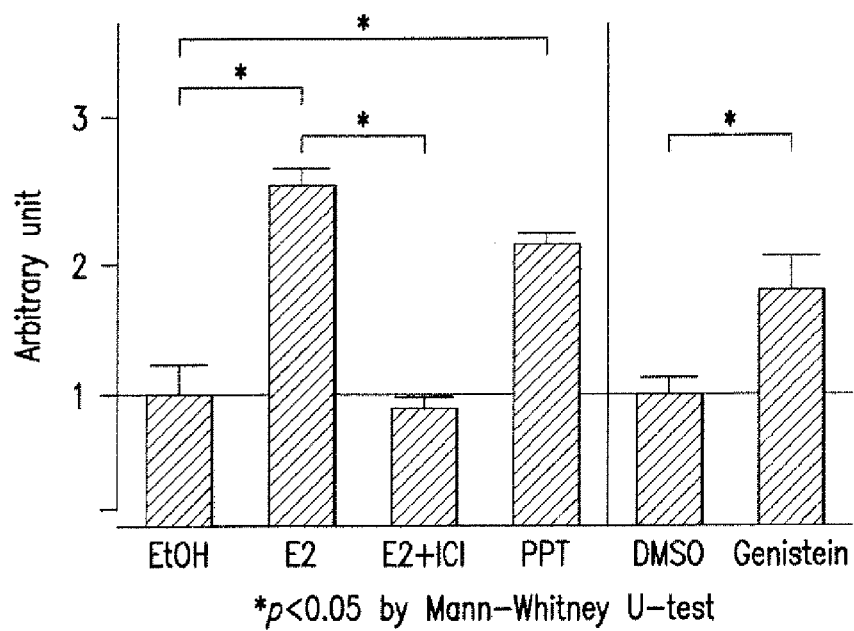

FIG. 8A-B. Estrogen and ER alpha agonist also induce collagen bundle thickening in ex vivo. Human skin samples were plated on to 6-well plate and treated with ethanol (EtOH), Estradiol (E2), estradiol with ICI (E2+ICI), PPT, DMSO, and genistein and incubated for 7 days. A. Hematoxylin and Eosin staining of explanted skin. Images were taken at 800× magnification. B. Summary of thickness of collagen bundles. Thickness of collagen bundles were measured and ratio of the thickenss compare with vehicle control (EtOH or DMSO) was calculated as an arbitrary unit. Summary of 3 experiments are shown in the figure. *p>0.05 by Mann-Whitney U-test.

Figure 9:
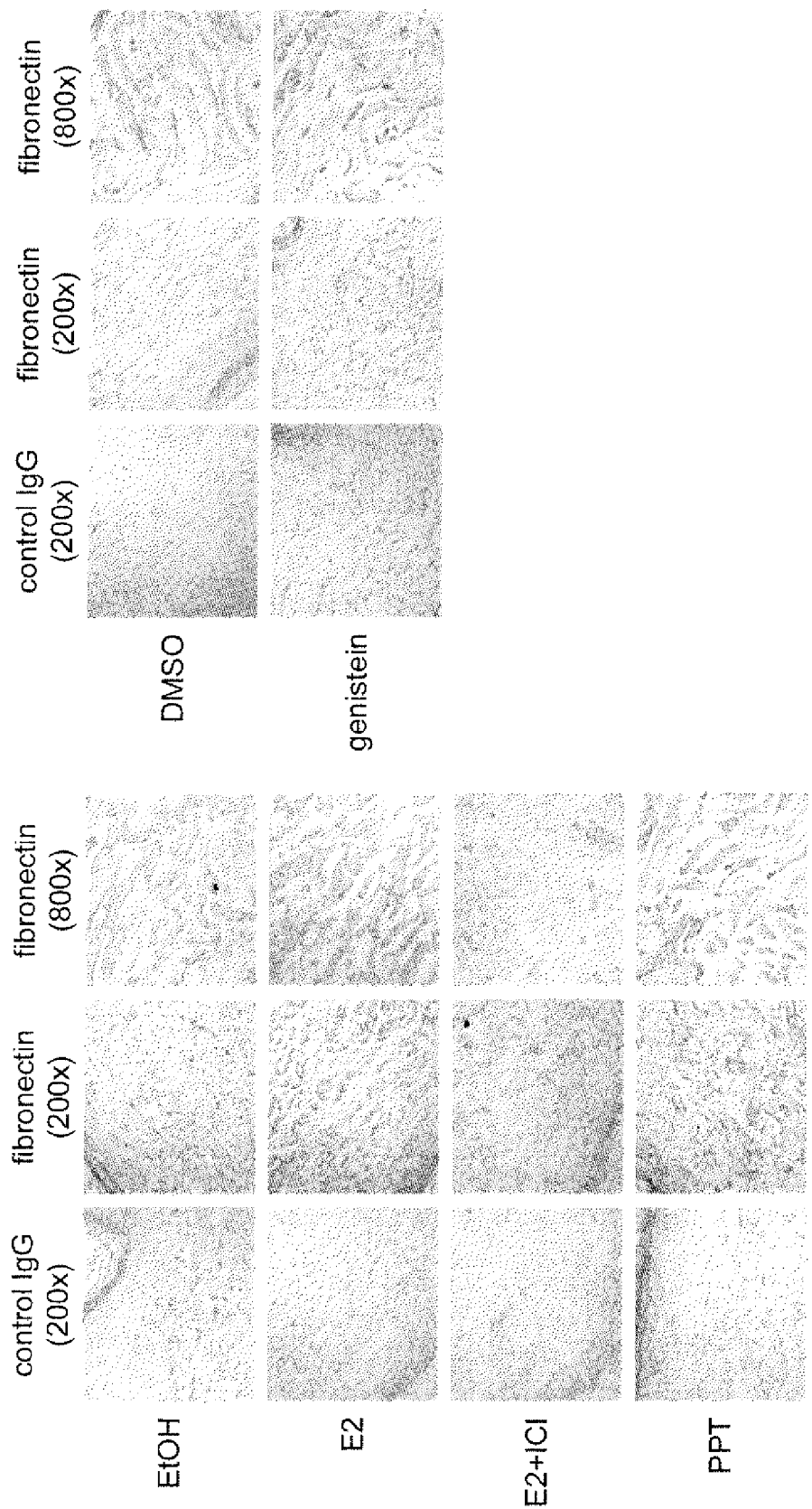

FIG. 9. Estrogen and ER alpha agonist induce fibronectin expression in ex vivo. Human skin samples were plated on to 6-well plate and treated with ethanol (EtOH), Estradiol (E2), estradiol with ICI (E2+ICI), PPT, DMSO, and genistein and incubated for 7 days. Immunohistochemistry was performed using anti-fibronectin antibody and visualized with AEC (red).

FIGS. 10A-G. Examples of ERANTS.

5. DETAILED DESCRIPTION OF THE INVENTION

For clarity of description, and not by way of limitation, the detailed description of the invention is divided into the following subsections:

(i) estrogen receptor antagonists;
(ii) estrogen receptor beta agonists;
(iii) sclerosing disorders; and
(iv) methods of treatment.

5.1 Estrogen Receptor Antagonists

Various estrogen receptor antagonists ("ERANTs") can be used according to the invention.

In certain non-limiting embodiments, an ERANT may exhibit little or essentially no detectable agonist activity.

The extent of agonist or antagonist activity may be evaluated by an assay known in the art, for example, but not limited to, the immature rodent uterotrophic assay, the ERα Redistribution® Assay (BioImage), the Ishikawa assay (proliferation of Ishikawa human endometrial tumor cells quantified using alkaline phosphatase), MCF-7 proliferation, estrogen-dependent transcription assays, kinetics studies performed using surface plasmon resonance biosensors (Biacore), FRET studies, etc, (42-49). Estrogen agonist activity, for example and not by way of limitation, includes the ability to stimulate proliferation of MCF-7 cells, the ability to promote uterine growth in the immature rat uterotrophic assay, the ability to stimulate proliferation of Ishikawa human endometrial tumor cells, and the ability to inhibit bone loss in ovarectomized rats.

Relative agonist/antagonist activities may (for example and not by limitation) be evaluated by administering the test compound together with a known ER agonist control and/or a known ER antagonist control and determining the impact of the test compound on the effect of the control compound. For example, using the MCF-7 cell proliferation assay, the effect of a test compound alone can be measured to determine agonist activity (e.g., the ability of the test compound to stimulate proliferation of the cells), and the effect of a test compound on proliferation induced by a known agonist (e.g., estradiol) may be used to assess the test compound's antagonist activity (e.g., the ability of the test compound to inhibit estradiol-induced proliferation).

"Little or essentially no" agonist activity, as that term is used herein, means that the level of agonist activity is deemed clinically insignificant (not reaching undesirable levels). In specific, non-limiting embodiments, an ERANT having little agonist activity exhibits an ED50 for agonist activity that is at least 1.5 fold greater, or two fold greater, or five fold greater, or ten fold greater than the ED50 for antagonist activity. An ERANT may be, but is not necessarily, specific to ER-α ("ERANT-α") or ER-β ("ERANT-β").

Figure 10A:
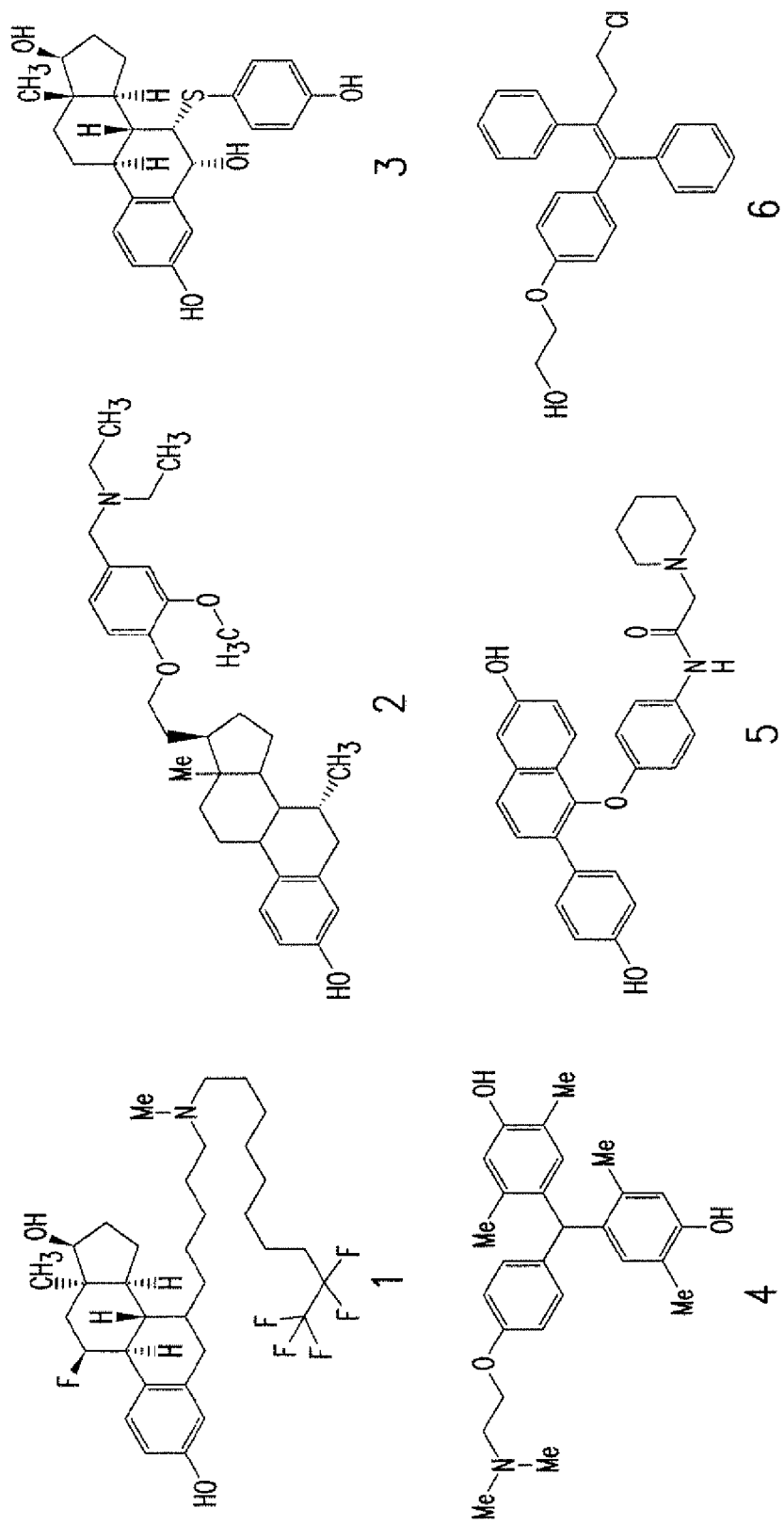
Figure 10B:
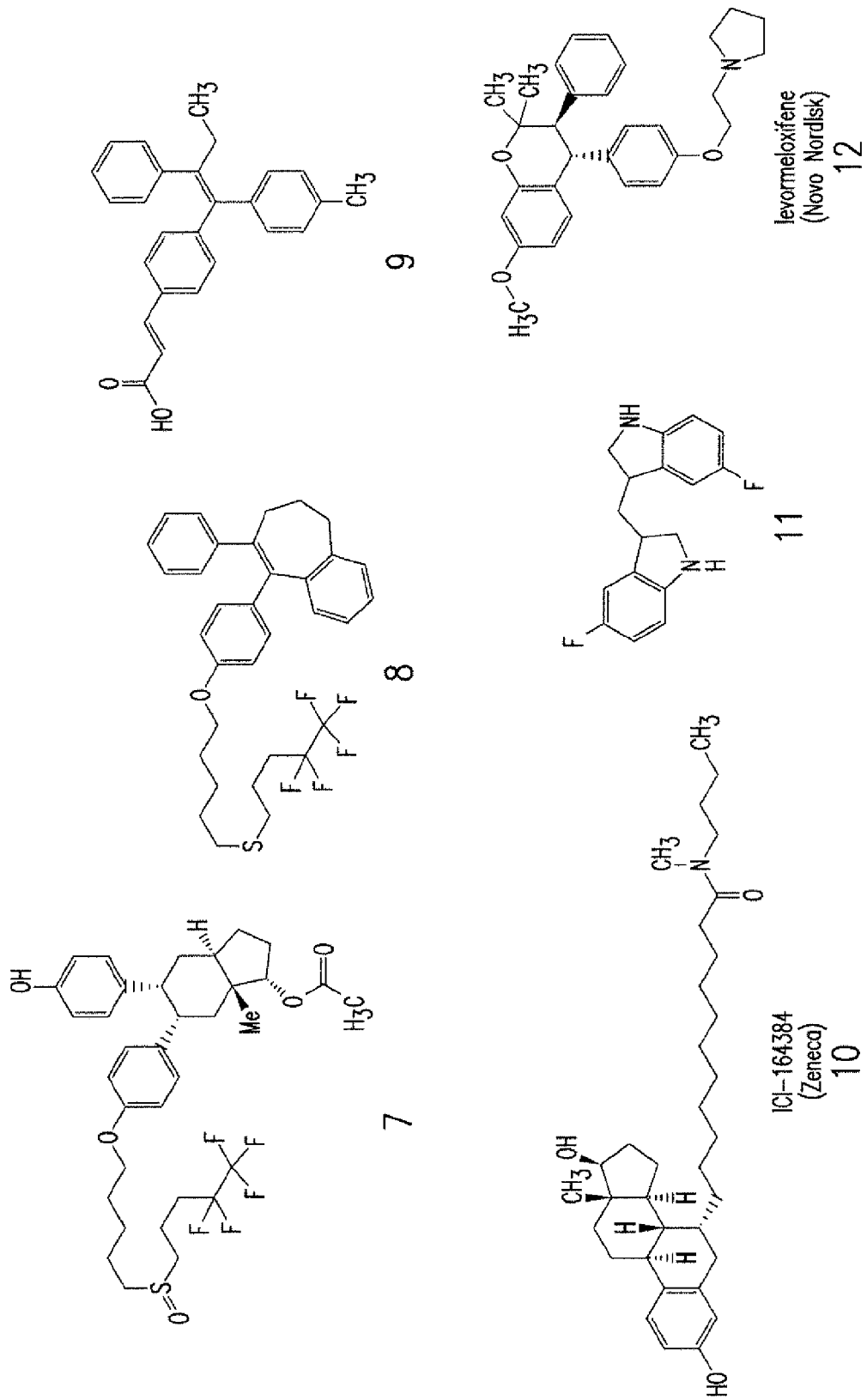
Figure 10C:
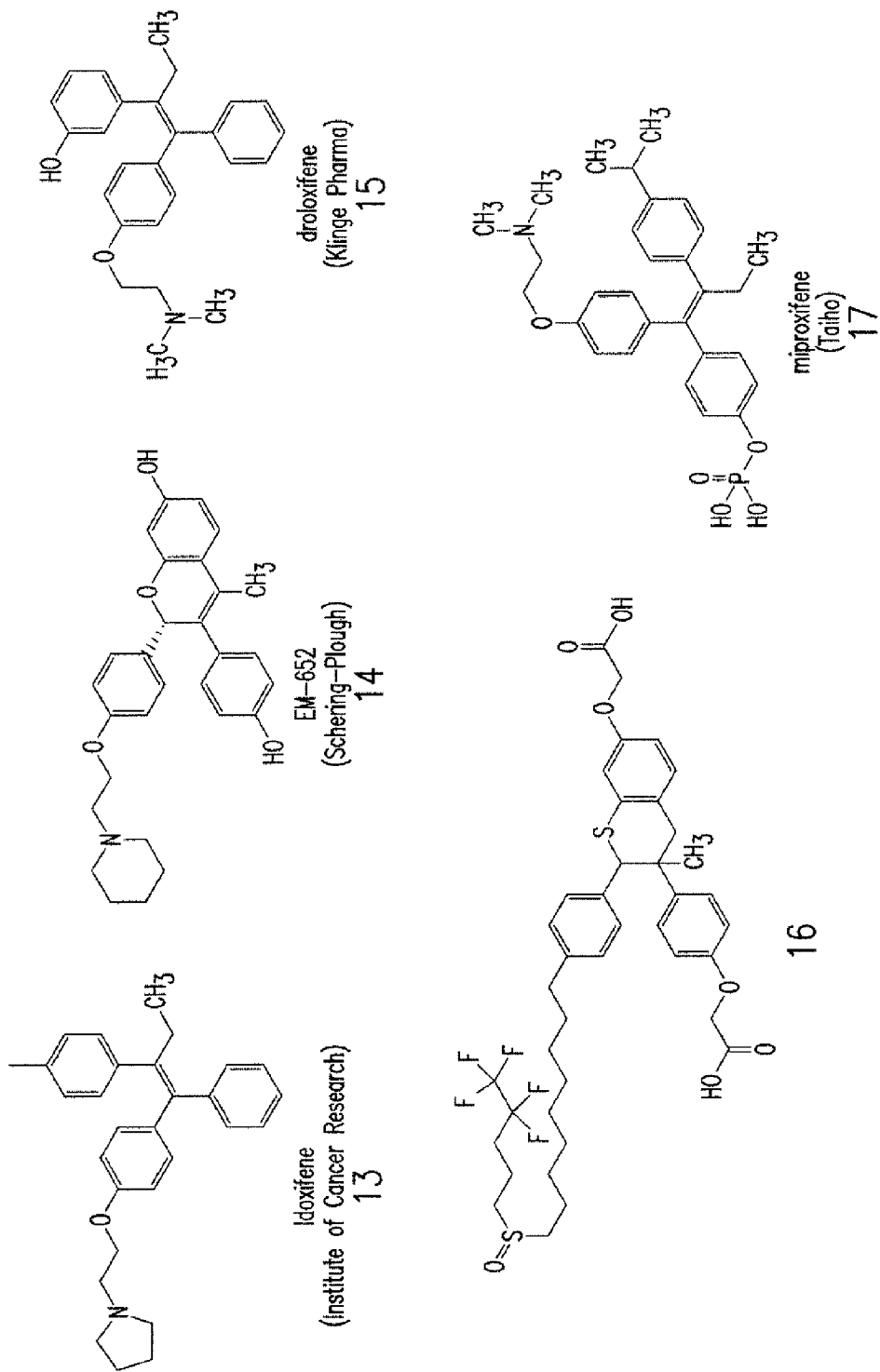
Figure 10D:
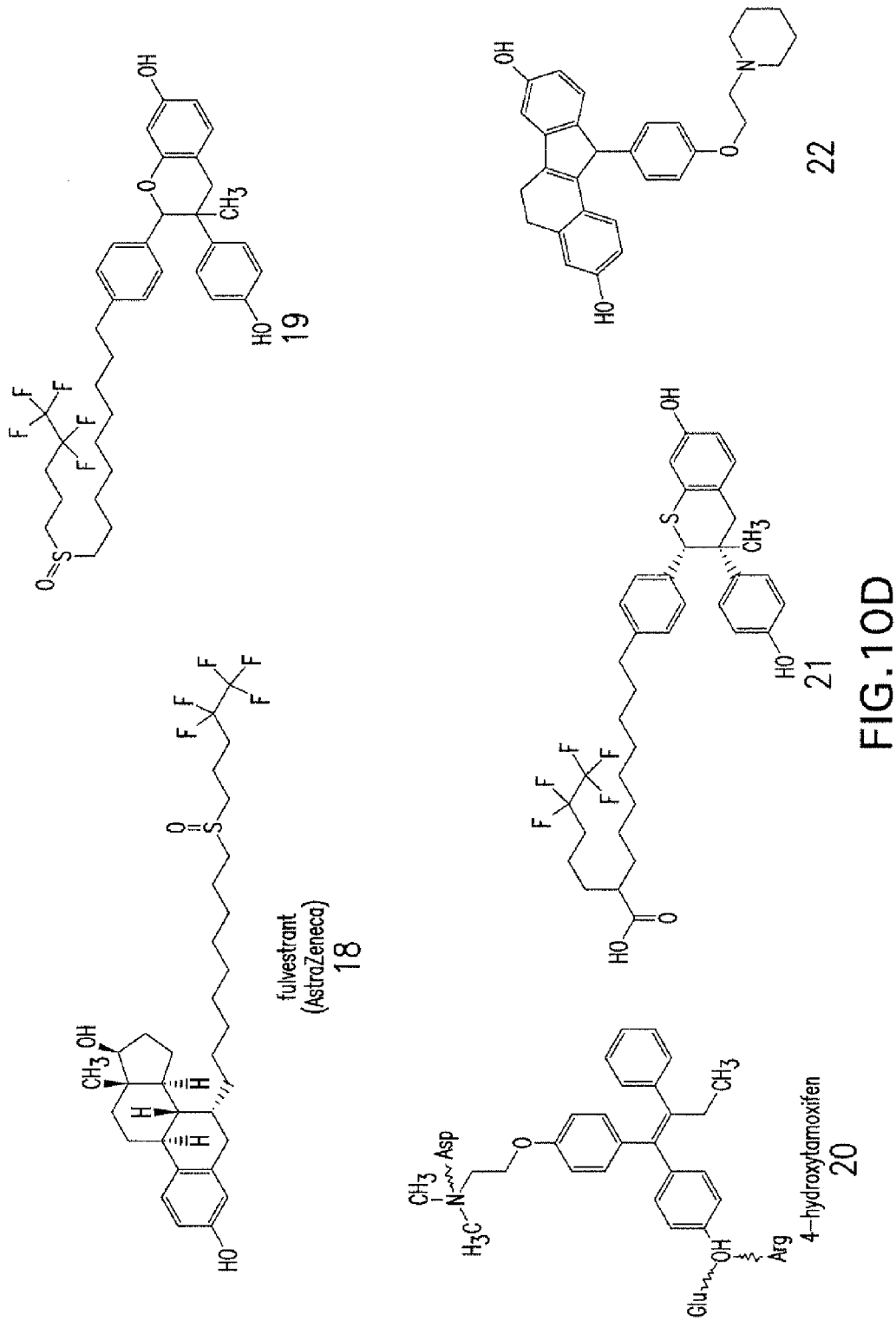
Figure 10E:
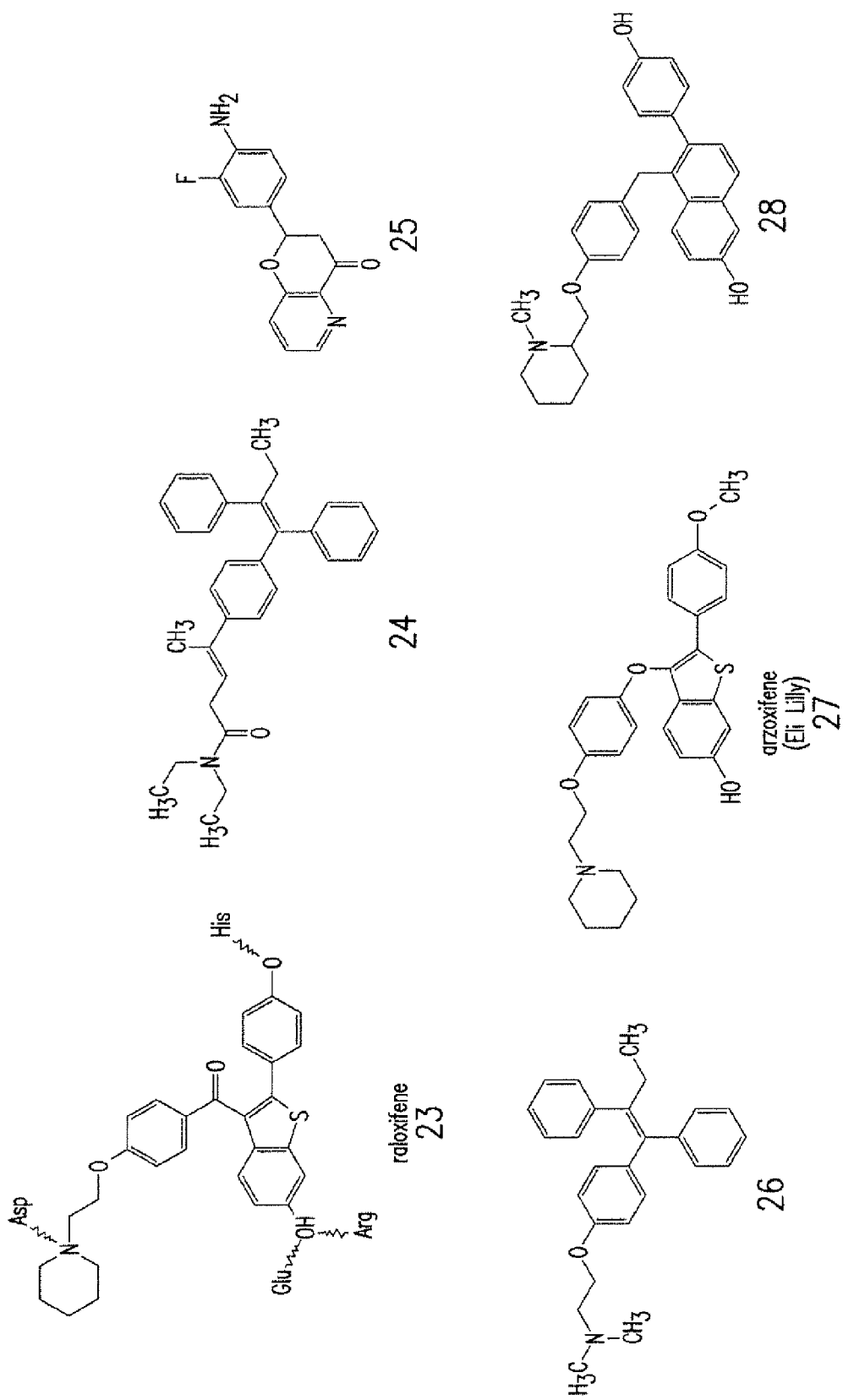
Figure 10F:
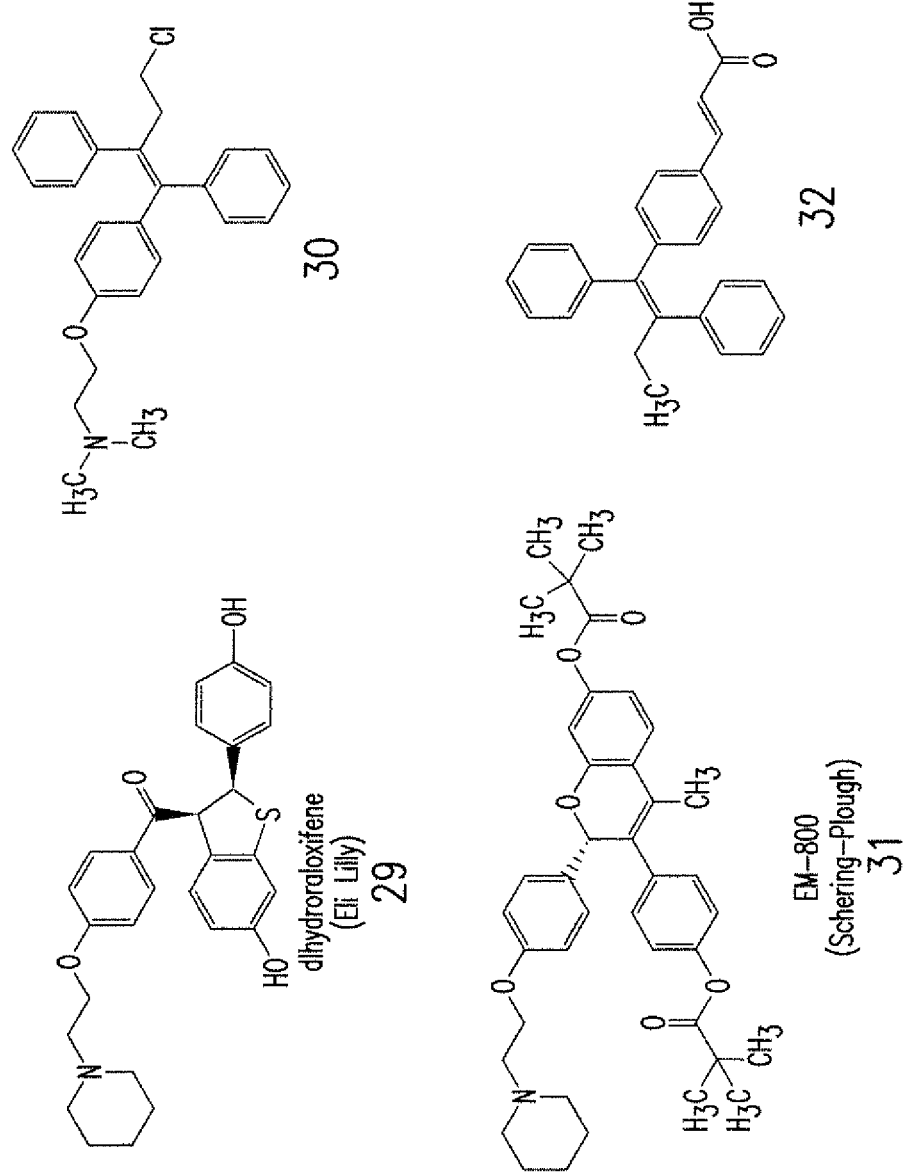
Figure 10G:
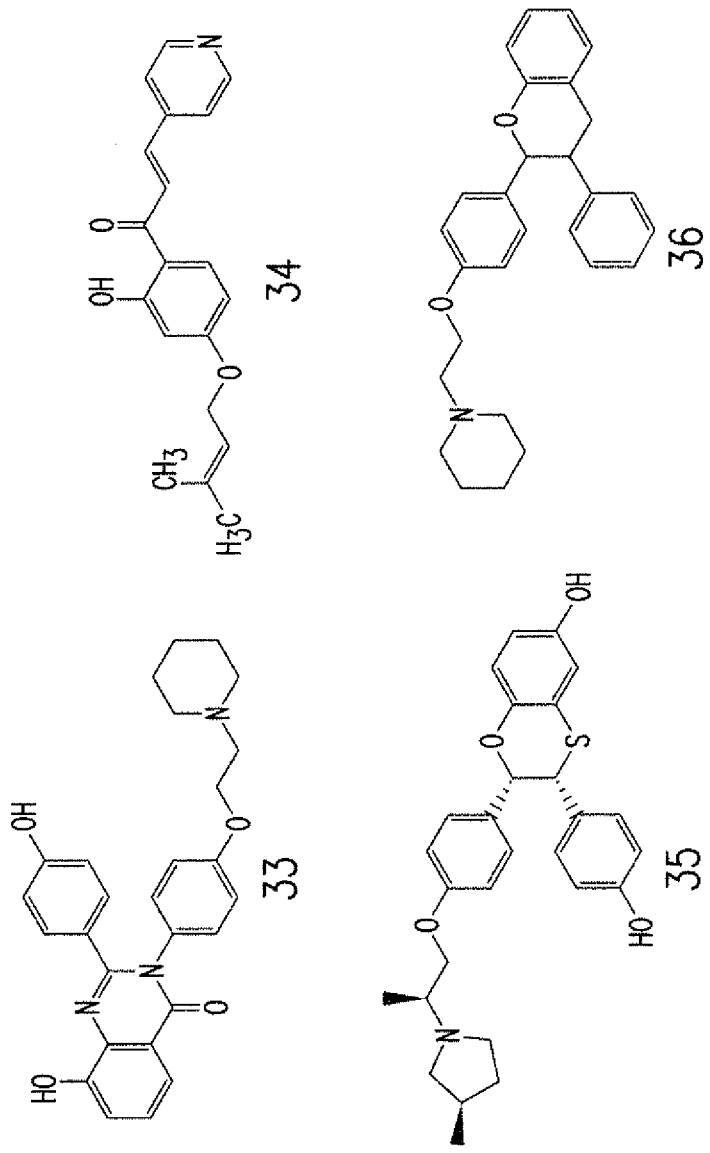

Non-limiting examples of ERANTs which exhibit little or essentially no agonist activity include fulvestrant (Faslodexe ICI 182,780), GW7604 (50), EM-800 (51), and compound 35 of FIG. 10G (52).

In certain non-limiting embodiments of the invention, the ERANT is an ERANT-α. Non-limiting examples of ERANT-αs include fulvestrant, 4-hydroxytamoxifen, basic side-chain pyrazoles such as methyl-piperidino-pyrazole (Sun et al., 2002, Endocrinol. 143(3):941-947) and theophylline, 8-[(benzylthio)methyl]-(7CI,8CI) (TPBM; Mao et al., 2008, J Biol Chem. 283(19):12819-30).

In further non-limiting embodiments, the present invention utilizes an ERANT which exhibits mixed ER agonist/agonist activity. "Mixed ER agonist/activity" means that the compound exhibits significant agonist and antagonist activity, even where different activities are observed under different conditions, and such compounds may act as antagonists of ERs in certain tissues and agonists of ERs in others.

Non-limiting examples of ERANTs which exhibit mixed agonist/antagonist activity include tamoxifen citrate, 4-hydroxy-tamoxifen, raloxifene hydrochloride, toremifene, GW-5638, arzoxifene, dihydroraloxifene, miproxifene, droloxifene, idoxifene, levormeloxifene, ICI-164384 and bazedoxifene.

Non-limiting examples of ERANTS which may be used according to the invention include those compounds depicted in FIG. 10A-C.

In an additional, non-limiting specific example, 2-methoxyestrogen (2-ME) may be used as an ERANT according to the invention.

Not by way of limitation, it may be desirable to evaluate whether an ERANT exhibits satisfactory properties for use according to the invention, e.g. by an assay system as described in the example section below. As non-limiting examples, the ability of an ERANT to inhibit estradiol-induced fibronectin expression could be evaluated in cell cultures of fibroblasts from normal subjects (see FIGS. 4 and 6) or from scleroderma patients, and/or the ability of an ERANT to inhibit fibronectin expression, reduce skin thickness, or reduce collagen bundle size could be tested in estradiol-treated skin explant cultures (see FIGS. 7A-B, 8A-B and 9). Moreover, such assays could be used to compare the potency of the ERANT relative to that of fulvestrant toward ascertaining therapeutic dose ranges.

In related non-limiting embodiments, an anti-estrogen compound which acts by a mechanism other than receptor antagonism may be used as a sole agent or in combination with an ERANT in the treatment of sclerosing disorders. Examples of anti-estrogen compounds which may be used according to the invention include aromatase inhibitors such as exemestane, anastrazole, letrozole, vorozole, formestane, and fadrozole.

5.2 Estrogen Receptor Beta Agonists

In further non-limiting embodiments of the invention, an ER-β agonist ("ERAG-β") may be used, either alone or in combination with an ERANT that is preferably selective for ERα. In specific non-limiting embodiments, the agonist acts at the ER-$β_2$ receptor, Non-limiting examples of ERAG-βs include, but are not limited to, genistein, ERB-041 (53, 54), WAY-202196 (53, 56), WAY-214156 (53), biochanin A (55), DPN, and as set forth in EP1448206, U.S. Pat. No. 7,442,812 and U.S. Pat. No. 7,279,499.

Not by way of limitation, it may be desirable to evaluate whether an ERAG-β-ERANT combination exhibits satisfactory properties for use according to the invention, e.g. by an assay system as described in the example section below. As non-limiting examples, the ability of an ERAG-β-ERANT combination to inhibit estradiol-induced fibronectin expression could be evaluated in cell cultures of fibroblasts from normal subjects (see FIGS. 4 and 6) or from scleroderma patients, and/or the ability of an ERAG-β-ERANT combination to inhibit fibronectin expression, reduce skin thickness, or reduce collagen bundle size could be tested in estradiol-treated skin explant cultures (see FIGS. 7A-B, 8A-B and 9). Moreover, such assays could be used to compare the potency of the ERAG-β-ERANT combination relative to that of fulvestrant toward ascertaining therapeutic dose ranges.

5.3 Sclerosing Disorders

The present invention provides for the treatment of sclerosing disorders, including, but not limited to, systemic sclerosis (scleroderma) and localized scleroderma such as morphea, and other disorders characterized by abnormal or excessive deposition of fibrous tissue, including, but not limited to, liver cirrhosis, glomerulonephritis, pulmonary fibrosis, subepithelial fibrosis in asthma, systemic fibrosis, rheumatoid arthritis, osteoartritis, familial multifocal fibrosclerosis, and aberrant wound healing.

5.4 Methods of Treatment

The present invention provides for a method for treating a sclerosing disorder comprising administering, to a subject in need of such treatment, an effective amount of an anti-estrogen composition comprising one or more agent selected from the group consisting of an ERANT, an ERAG-β, and a non-receptor based anti-estrogen (such as an agent that inhibits estrogen synthesis, for example a steroid aromatase inhibitor), Suitable agents in each of these categories are set forth above.

In particular non-limiting embodiments, the present invention provides for a method of treating a sclerosing disorder comprising administering, to a subject in need of such treatment, an effective amount of an ERANT. In preferred non-limiting embodiments, the ERANT is fulvestrant.

A subject in need of such treatment may be a human or a non-human subject and particularly, but not by way of limitation, may be a female. The subject may be suffering from or at risk of developing a sclerosing disorder, for example but not by way of limitation, as a result of age, family history or exposure to a toxic agent.

The agents of the invention may be administered intramuscularly, intravenously, intraperitoneally, subcutaneously, intradermally, intranasally, intratracheally, by inhalation, orally, rectally, vaginally, or by any other standard route of administration. Where the agent is fulvestrant, intramuscular or intravenous administration is preferred, with intramuscular administration most preferred.

Doses of the agent or agents may be administered daily, weekly, every two weeks, monthly, every six weeks, every two months, or at any other period which permits the maintenance of effective drug levels.

The treatment period may be continuous or discontinuous.

"Treating" a sclerosing disorder means at least inhibiting the rate of progression of the disorder, as marked by clinical signs and symptoms, including hardening of the skin and tissues, for example thickening of the dermis, pulmonary fibrosis, hepatic fibrosis, pulmonary hypertension, and hepatic hypertension, and may also mean prolonging survival of a patient suffering from the disorder.

In particular non-limiting embodiments, where the agent is the ERANT fulvestrant, a dosage of between about 100-500 mg may be administered intramuscularly to a subject at an interval of about one to two weeks, inclusive.

In alternative particular non-limiting embodiments, where the agent is the ERANT fulvestrant, a dosage of between about 100-500 mg may be administered intravenously to a subject at an interval of about one to two weeks or at an interval of about one to two months, inclusive.

In further particular non-limiting embodiments, where the ERANT is an agent other than fulvestrant, the dosage of that agent may be calculated as {(between about 100-500 mg) multiplied by the ratio of the IC50 of the agent to the IC50 of fulvestrant in a standard assay of estrogen antagonist activity (for example, the IC50 for fulvestrant in the MCF7 proliferation assay is approximately 14 nM/L (56)}, where said dosage may be administered at an interval as set forth above for the intramuscular or intravenous administration of fulvestrant adjusted according to the serum half life of the agent relative to fulvestrant (which has a half life of approximately forty days).

In a specific, non-limiting embodiment, fulvestrant may be administered at a dosage of 250 mg about every four weeks.

In another specific, non-limiting embodiment, fulvestrant may be administered first at a dosage of 250 mg-1 g, preferably 500 mg, intramuscularly as a loading dose, followed by 250 mg intramuscularly about two weeks later, followed by another 250 mg dose about two weeks after that, with maintenance therapy 250 mg intramuscularly about every four weeks.

"About" as used herein means plus or minus twenty percent.

The above dosage regimens of ERANT may optionally be combined with an effective dose of ERAG-β and/or other anti-estrogen compound.

6. EXAMPLE

The Effects of Estradiol on Extracellular Matrix Production Ex Vivo in Human Skin and In Vitro in Skin Fibroblasts from Patients with Systemic Sclerosis and Their Normal Twins 6.1 Patients and Methods Source of Fibroblasts.

Skin-punch biopsies (6 mm) were obtained with informed consent from the clinically affected and unaffected skin of 6 patients with SSc and 5 healthy twins. All SSc patients had diffuse skin involvement and met the American College of Rheumatology criteria for the diagnosis of SSc (1). Biopsies were performed on the leading edge of dermal thickening and clinically normal skin. The skin samples were minced, placed in 60-mm tissue culture dishes and cultured at 37° C. in a humidified atmosphere in Dulbecco's modified Eagle's medium (DMEM) (Cellgro, Herndon, Va.) supplemented with 10% fetal bovine serum (FBS; Sigma-Aldrich, St. Louis, Mo.), 100 IU/ml penicillin, and 100 µg/ml streptomycin (Invitrogen, Carlsbad, Calif.).

Treatment of Cells with 17-β-estradiol (E2), ER Ligands and E2 Signaling Inhibitors.

Skin fibroblasts ($2 \times 10^5$ cells per well) were seeded in 35 mm cell culture dishes in DMEM/10% FBS. The following day, the medium was replaced with phenol-red free DMEM (Cellgro) without serum for 24 hours to deprive the cells of estrogen. Fresh phenol-red free DMEM plus 10% charcoal stripped fetal bovine serum (Hyclone, Logan, Utah) was added with one of the following: ethanol as vehicle control (0.1%) or E2 (10 nM; Sigma-Aldrich) for 24 hours (for RNA extraction) or 48 hours (for protein extraction). TGF-β (10 ng/ml; R&D systems, Minneapolis, Minn.) was used as a positive control. ICI 182,780 (100 nM; Tocris, Ballwin, Mo.), pure ER antagonist, and signaling inhibitors (MEK inhibitor U0126, PI3K inhibitor LY294002 and p38 MAPK inhibitor SB202190 (10 μM each; Cell Signaling Technology, Beverly, Mass.) were added where indicated. To determine the role of ERα and β on FN individually, cells we cultured with propyl-pyrazole-triol (PPT), an ERα specific ligand (100 nM; Tocris), and genistein, an ERβ specific ligand (100 nM; Sigma-Aldrich), under similar conditions used for E2 treatment.

Extracellular Matrix Extraction.

Extracellular matrix (ECM) was extracted as we have previously described. (35) Briefly, cells were rinsed with PBS and incubated with 8M Urea in PBS for 20 mins. Cells were aspirated and the ECM was rinsed three times with PBS. ECM was scraped in 100 μl sample buffer (20 mM dithiothreitol, 6% SDS, 0.25 M Tris, pH 6.8, 10% glycerol, 10 mM NaF and bromophenyl blue) and analyzed by western blot.

RNA Isolation and RT-PCR.

Skin fibroblasts in early passage (passages 3-4) were harvested and RNA was extracted using TRIzol (Invitrogen). mRNA was reverse transcribed using Superscript II (Invitrogen) following the manufacturer's recommendations. The cDNA generated was used as a template for amplification by PCR with primers specific for ERα 5'-TGGGAATGAT-GAAAGGTGGGAT-3' (SEQ ID NO:1) and 5'-AGGGAT-TATCTGAACCGTGTG-3'(SEQ ID NO:2), ERβ 5'-TGTGGGTACCGCCTTGTGC-3'(SEQ ID NO:3) and 5'-GGGCCAGTTCACCTCAG-3' (SEQ ID NO:4), Fibronectin, 5'-ACCGTGTGGTACAGGTG-3' (SEQ ID NO:5) and 5-GTCACAGAGGCTACTAT-3 (SEQ ID NO:6) and β-actin, 5'-ATGTTTGAGACCTTCAACAC-3'(SEQ ID NO:7) and 5'-CACGTCACACTTCATGATGG-3' (SEQ ID NO:8). PCR amplification was performed in a 50 μl reaction containing 10 units of the reverse transcription reaction, Taq DNA polymerase (Invitrogen), 10×PCR buffer (750 mM Tris-HCl, pH8.8, 200 mM $(NH4)_2SO_4$ and 0.1% Tween 20), 1.5 mM $MgSO_4$, 1 mM of each deoxynucleotide triphosphate in a Peltier Thermal Cycler-200 (MJ Research, Waltham, Mass.). Conditions were an initial denaturation at 95° C. for 4 min, followed by 35 cycles of 94° C. for 45 sec, 55° C. for 30 sec, and 68° C. for 2 min. Final extension was at 68° C. for 5 min. 20 μl of each reaction was electrophoresed on a 1% agarose gel in 1×TAE (Tris/acetate/EDTA) buffer and products were visualized following staining with ethidium bromide. Molecular weight of each PCR product: ERα 1062 bp, ERβ 934 bp, FN 513 by and β-actin 494 bp.

Protein Extraction and Western Blot.

Cells were grown to confluency in 35 mm culture dishes. Cells were rinsed with 1×PBS and scraped in sample buffer (20 mM dithiothreitol, 6% SDS, 0.25 M Tris, pH 6.8, 10% glycerol, 10 mM NaF and bromophenyl blue). Samples were separated by electrophoresis on 8% SDS-polacrylamide gels (National Diagnostic, Atlanta, Ga.) and transferred to nitrocellulose membranes. Membranes were blocked with 5% non-fat milk in 1×TBS-Tween20 (0.2 M Tris, 0.14 M NaCl, 0.1% Tween 20), followed by incubation with mouse monoclonal anti-human EDA-fibronectin antibody, rabbit polyclonal anti-human fibronectin antibody, rabbit polyclonal anti-ERα antibody, rabbit polyclonal anti-ERβ antibody (Santa Cruz Biotechnology, Santa Cruz, Calif.), mouse monoclonal anti-human vitronectin, mouse monoclonal anti-β-actin (Sigma-Aldrich), or mouse monoclonal anti-GAPDH (Ambion, Austin, Tex.) in 1×TBS-Tween20 followed by horseradish peroxidase-conjugated donkey anti-rabbit IgG (Amersham, Piscataway, N.J.) or donkey anti-mouse IgG (Amersham). Immunoreactive proteins were detected by chemiluminescence (PerkinElmer Life Sciences, Boston, Mass.), followed by autoradiography.

Measurement of Skin Dermal and Collagen Bundle Thickness.

Dermal and collagen bundle thickness were measured in skin sections stained with hematoxylin and eosin.

Dermal thickness was defined as the distance from the granular layer to the junction between the dermis and subcutaneous fat. Images were taken on a Nikon Eclipse 800 microscope (Nikon Instruments, Inc., Huntley, Ill.) using identical camera settings and ImageJ was used to measure thickness. Thickness was measured in 5 random fields in each sample.

Immunohistochemistry.

6 μm sections of paraffin-embedded skin tissues were de-paraffinized, endogenous peroxidase was quenched using 10% $H2O2$, and endogenous biotin was blocked using the biotin blocking kit (Dakocytomation, Carpinteria, Calif.). Sections were blocked with 5% serum and incubated with anti-fibronectin antibody followed by secondary antibody. Bound secondary antibody was detected using the AEC Red kit. A light hematoxylin counterstain was used to identify nuclei. Images were taken on a Nikon Eclipse 800 microscope.

6.2 Results

ERα and ERβ mRNA Expression in Fibroblasts from Twins Discordant for Ssc.

We examined ERα and ERβ mRNA expression levels in dermal fibroblasts from SSc patients and their healthy twins. The twins have been previously described (4,5). The expression level of ERα was modestly higher in fibroblasts from SSc patients compared to fibroblasts from their healthy twins (FIG. 1). Interestingly, the ERα levels in fibroblasts from affected skin fibroblasts were higher than unaffected skin fibroblasts in all samples except one (4A). Steady-state mRNA levels of ERβ were detected in fibroblasts from 5/6 healthy twins and 2/6 SSc patient fibroblasts (FIG. 1).

The Effect of E2 on Fibronectin mRNA and Protein Levels.

Primary fibroblasts from SSc patients and their healthy twins were cultured in the presence of E2 for 24 hrs (for mRNA) and 48 hrs (for protein). The effect of E2 on fibronectin (FN) expression was examined using RT-PCR and western blot analysis. FN mRNA and protein levels in SSc patient fibroblasts were higher than those in their healthy twins. E2 increased FN mRNA and protein levels in healthy twin and SSc fibroblasts (FIGS. 2A, 2B). E2 increased FN mRNA and protein levels in a time- and dose-dependent manner (FIGS. 3A, 3B). E2-induction of FN was detected in the cell supernatant and in the ECM (FIGS. 3A, 3B). E2 induced production of total FN and EDA-domain containing matrix FN (FIG. 3A). The induction of FN production and deposition by E2 was dose-dependent (FIG. 3B). The ER antagonist ICI 182, 780 blocked the effect of E2 on FN mRNA and protein expression but did not affect TGF-β-induced FN levels (FIG. 4).

Signaling Pathways Mediating the Effects of E2 on FN Induction.

To investigate the mechanism mediating E2 induction of FN, we pre-treated skin fibroblasts with vehicle, MEK inhibitor, PI3K inhibitor or p38 MAPK inhibitor for 1 hr prior to the addition of E2. FN protein levels were assessed by western blot analysis 48 hrs post-treatment. PI3K inhibitor and p38 MAPK inhibitor attenuated the E2-mediated increase of FN. MEK inhibitor had a more modest effect on E2 induction of FN. We also examined the effect of the chemical inhibitors on ERα and ERβ. ERα was increased by E2 and this increase was blocked by PI3K inhibitor, p38 MAPK inhibitor and MEK inhibitor. There was no significant difference in the expression of ERβ under the same conditions (FIG. 5).

The Effect of ER Ligands on FN Expression.

To assess the individual effect of ERα and/or ERβ on FN expression, we used PPT, an ERα ligand, and genistein, an ERβ ligand. Primary fibroblasts were treated with vehicle, E2, PPT or genistein for 48 hrs. Cell culture supernatants and ECM were harvested and analyzed by western blot. Vitronectin was detected as an ECM loading control. E2 and PPT increased FN protein levels in the ECM (FIG. 6). Genistein modestly increased FN protein levels (FIG. 6). Vitronectin levels were not modulated by any of the treatments.

Estradiol and Estrogen Receptor Alpha Agonist Induce Increased Dermal and Collagen Bundle Thickening and Fibronectin Deposition.

To further examine the effect of estradiol in skin tissues, dermal and collagen bundle thickness in dermis were assessed using an ex vivo organ culture system. Ex-planted skin tissues on 35-mm well plates were treated with estradiol, estrogen receptor alpha or beta agonists (PPT, genistein, respectively) or vehicles (ethanol for estraditol, PPT, DMSO for genistein, respectively) for 7 days, and skin sections were stained with hematoxylin and eosin. As shown in FIGS. 7A, 7B, 8A and 8B, estradiol and PPT induced an increase of dermal and collagen bundle thickness compared with vehicle (dermis: 1.61±0.12, p<0.05, 1.54±0.05, p<0.05, respectively, collagen bundles: 2.62+0.18, p<0.05, 1.84+0.15, p<0.05, respectively), and ICI 182,780 blocked the effect of estradiol. On the other hand, genistein did not induce thickening of dermis and collagen bundles. We also assessed the extent of deposition of fibronectin using immunohistochemistry. As shown in FIG. 9, the results of fibronectin deposition in collagen bundles were similar to those of thickness of skin and collagen bundles. Thus, estradiol is an important factor for the induction of skin fibrosis, and the effect of estradiol is mediated by estrogen receptor alpha, 6.3 Discussion The results presented herein indicate a role for E2 in the induction of FN in both SSc and normal skin fibroblasts. It has been previously demonstrated that E2 increases collagen during wound healing (28,29). E2 also increases FN mRNA in cardiac fibroblasts and has been associated with ECM remodeling (30). However, the mechanism(s) mediating the effect of E2 on FN expression are poorly understood.

SSc is more frequent in women than in men and the female: male ratio further increases to 10:1 during the child-bearing years (1, 3). E2 levels in women in child-bearing years is significantly higher than those of postmenoposal women. The menstrual cycle has four phases (menstrual, follicular, ovulation and luteal phase) and each phase corresponds to different circulating levels of E2 (32). E2 levels during the ovulation phase are 490-1710 pmol/l (mean 1087 pmol/l) and exceed levels detected during the other phases (33). E2 levels in postmenoposal women are 2-18 pg/ml (mean 7.6 pg/ml) (34). This is equivalent to 28 pmol/l and significantly lower than levels in women of child-bearing age. Therefore, circulating E2 levels are increased in the age range during which the SSc female:male ratio is highest.

ERα and ERβ are expressed in skin fibroblasts (7). ERα is located mainly in the cytoplasm of cells, but is also detected in the nucleus. ERβ is mainly localized to the nucleus. Our data confirm the expression of ERα and ERβ in primary dermal fibroblasts. Our results further confirm increased expression of ERα in affected SSc skin fibroblasts compared to unaffected skin fibroblasts from the same patients. We further show that propyl-pyrazole-triol (PPT), an ERα specific ligand, increases FN production. Moreover, ERα is increased by E2-treatment of skin fibroblasts. These results suggest that ERα is the main regulator of E2-mediated FN expression in dermal fibroblasts. Interestingly, ERβ levels were much lower in SSc patient fibroblasts than healthy twin fibroblasts although ERα was similarly expressed in SSc patient and healthy twin fibroblasts. ERβ expression is decreased in colon and prostate cancers and its reduced expression is related to tumor cell dedifferentiation (8-13). Global antagonism of ERα transcriptional activity by ERβ has been reported (14). ERβ directed repression of several ERα-mediated effects including fat reduction and cellular proliferation in the uterus and prostate (14). We demonstrated increased ERα and decreased ERβ expression in SSc. We further show that E2, activating via ERα, exerts pro-fibrotic effects. Taken together, these findings suggest that ERβ could play a protective role in SSc.

ER Acts as a Ligand-Activated Transcription Factor.

The classical mechanism of ER action involves estrogen binding to nuclear receptors followed by receptor dimerization and binding to specific response elements known as estrogen response elements (EREs) located in the promoters of target genes. Dimerized receptors can also bind other transcription factors such as AP-1 and SP-1 (15-17). Estrogens exert some of their effects through the action of ERs on gene expression, but a number of other effects of estrogens are so rapid that they cannot rely on the activation of RNA or protein synthesis. These actions are known as nongenomic actions and are believed to be mediated through membrane associated ERs. Most endogenous plasma membrane ERs exist as homodimers in the presence of E2 (6) and mediate rapid E2 activation of a number of signaling cascades including cyclic AMP, inositol-1.4.5-triphosphate (PI3K), phospholipase C, and MAP kinase (18). These signaling pathways regulate cytokine production, apoptosis, cell-cycle arrest, regulation of RNA splicing or stabilization, and tumor cell differentiation (22, 23). The MAPK superfamily consists of three well-characterized subfamilies (19). ERKs respond to growth factors or other external mitogenic signals and are involved in promoting cell proliferation. The p38 MAPK and c-Jun N-terminal kinase (JNK) pathways are distinguished by generally being activated in response to stress and are thus called the stress-activated kinases that promote inflammation and programmed cell death (20, 21). PI3K also has an important role in mitosis, apoptosis, motility, proliferation, and differentiation. It is not surprising, therefore, that tumorigenesis, immune responses, cell survival and other biological functions are regulated by PI3K (27). We have demonstrated that all three kinases (ERK MAPK, p38K MAPK and PI3K) regulate E2 signaling and its induction of FN expression with FN induction being mainly regulated by PI3K and p38 MAPK and to a lesser extent by ERK MAPK. PI3K and p38 MAP kinases have also been reported to regulate E2/ER's antiapoptotic action on cardiomyocytes (23). Our findings support the role of these E2 signaling cascades in skin fibroblasts and in the regulation of ECM production.

We had previously shown that human skin maintained in an organ culture system can be used to recapitulate in vivo events and to test the efficacy of anti-fibrotic agents (58). The present data demonstrate that E2 can exert pro-fibrotic activity ex vivo in human skin and that this effect can be specifically blocked by ICI 182,780. This supports the applicability of these findings to human disease and the potential therapeutic effects of ICI 182,780 for human fibrosis.

In conclusion, we have detected differential expression of ERα and ERβ in SSc patients. We have also identified E2 as an inducer of FN expression in skin fibroblasts obtained from SSc patients and healthy donors. The effects of E2 on FN were mainly regulated via ERα and the E2/ER downstream signaling cascades, PI3K and p38 MAPK. We also demonstrated that E2 is fibrotic ex vivo and that ICI can be used effectively to inhibit dermal fibrosis. The pro-fibrotic effect may explain, at least in part, the higher frequency of SSc in women, especially during the child-bearing years.

7. EXAMPLE

Serum Levels of Estrogens are Increased in Post-Menopausal Scleroderma Patients The forms of estrogen that act in the body are: estradiol, estrone, and estriol. Estradiol is the most potent whereas estriol is the least potent.

Levels of estradiol and estrone were measured in the sera of female patients with scleroderma who were post-menopausal and were compared to levels measured in post-menopausal controls. Neither group was on hormone replacement therapy. Measurements were done by mass spectrometry in the Small Biomolecule Core in the School of Pharmacy of the University of Pittsburgh. Estradiol levels were found to be elevated in the serum of post-menopausal patients with scleroderma who are not on hormone replacement therapy: 6.11±2.08 pg/ml in controls vs. 7.43±5.94 pg/ml in patients with systemic sclerosis ($p<0.01$). Additionally, the levels of estrone were also found to be significantly elevated in the sera of patients with scleroderma who are post-menopausal: 27.28±17.85 pg/ml in controls vs. 56.66±54.94 pg/ml in patients with systemic sclerosis ($p=0.007$). These findings are consistent with a role for estrogen in the etiology of scleroderma.

8. REFERENCES

1. Silver R M, Medsger T A Jr, Bolster M B. Sysremic sclerosis and scleroderma variants: clinical aspects. In: Koopman W J, Moreland L W, editors. Arthritis and allied conditions. Philadelphia: Lippincott, Williams & Wilkins; 2005. p. 1633-80.
2. Highland K B, Silver R M. New developments in scleroderma interstitial lung disease. Curr Opin Rheumatol 2005; 17:734-45.
3. Deroo B J, Korach K S. Estrogen receptors and human disease. J Clin Invest 2006; 116:561-70.
4. Feghali-Bostwick C, Medsger T A Jr, Wright T M. Analysis of systemic sclerosis in twins reveals low concordance for disease and high concordance for the presence of antinuclear antibodies. Arthritis Rheum 2003; 48:1956-63.
5. Zhou X, Tan F K, Xiong M, Arnett F C, Feghali-Bostwick C A. Monozygotic twins clinically discordant for scleroderma show concordance for fibroblast gene expression profiles. Arthritis Rheum 2005; 52:3305-14.
6. Razandi M, Pedram A, merchenthaler I, Greene G L, Levin E R. Plasma membrane estrogen receptors exist and functions as dimers. Mol Endocrinol 2004; 18:2854-65.
7. Haczynski J, tarkowski R, Jarzabek K, Slomczynska M, Wolczynski S, Magoffin D A, JAkowicki J A, JAkimiuk A J. Human cultured skin fibroblasts express estrogen receptor alpha and beta. Int J Mol Med 2002; 10(2):149-53.
8. Foley E F, Jazaeri A A, Shupnik M A, Jazaeri O, Rice L W. Selective loss of estrogen receptor beta in malignant human colon. Cancer Res 2000; 60:245-48.
9. Jassam N, Bell S M, Speirs V, Quirke P. Loss of expression of oestrogen receptor beta in colon cancer and its association with Duke's staging. 2005; 14:17-21.
10. Konstantinopoulos P A et al. Oestrogen receptor beta (ER beta) is abundantly expressed in normal colonic mucosa, but declines in colon adenocarcinoma paralleling the tumor's dedifferentiation. Eur J Cancer 2003; 39:1251-58.
11. Campbell-Thompson M, Lynch I J, Bhardwaj B. Expression of estrogen receptor (ER) subtypes and ERbeta isoforms in colon center. Cancer Res 2001; 61:632-40.
12. Leav I, Lau K M, Adams J Y, McNeal J E, Taplin M E, Wang J, Singh H, Ho S M. Comparative studies of the estrogen receptors beta and alpha and the androgen receptor in normal human prostate grands, dysplasia, and in primary and metastatic carcinoma. Am J Pathol 2001; 159: 79-92.
13. Horvath L G et al. Frequent loss of estrogen receptor-beta expression in prostate cancer. Cancer Res 2001; 61:5331-35.
14. Weihua Z, Makela S, Andersson L C, Salmi S, Saji S, Webster J I, Jensen E V, Nilsson J, Warner M, Gustafsson J A. A role for estrogen receptor b in the regulation of growth of the ventral prostate. Proc Natl Acad Sci 2001; 98:6330-35.
15. Nilsson S, Makela S, Treuter E, Tujague M, Thomsen J, Andersson G, Enmark E, Petterson K, Warner M, Gustafsson J A. Mechanisms of estrogen action. Physiol Rev 2001; 81:1535-65.
16. O'Lone R, Frith M C, Karlsson E K, Hansen U. Genomic targets of nuclear estrogen receptors. Mol Endocrinol 2004; 18:1859-1875.
17. Gottlicher M, Heck S, Herrlich P. Transcriptional crosstalk, the second mode of steroid hormone receptor action. J Mal Med 1998; 76:480-89.
18. Levin E R. Cellular functions of plasma membrane estrogen receptors. Steroid 2002; 67:471-75.
19. Chang L, Karin M. Mammarian MAP kinase signaling cancades. Nature 2001; 410:37-40.
20. Xia Z, Dickens M, Raingeaud J, Davis R J. Opposing effects of ERK and JNK-p38 kinases in apoptosis. Science 1995; 270:1326-31.
21. Gaicheva-Galgova Z, Derijard B, Wu I H, Davis R J. An osmosensing signal transduction pathway in mammalian cells. Science 1994; 265:806-08.
22. Olson J M, Hallahan A R. P38 MAP kinase: a concergence point in cancer therapy. Trends Mol Med 2004; 10:125-29.
23. Kim J K, Levin E R. Estrogen signaling in the cardiovasucular system. Nucl Res Signaling 2006; 4:1-5.
24. Beretta L, Caronni M, Origgi L, Ponti A, Santaniello A, Scorza R. Hormone replacement therapy may prevent the development of isolated pulmonary hypertension in patients with systemic sclerosis. Scand J Rheumatol 2006; 35: 468-71.
25. Thomas-Golbanov C K, Wilke W S, Fessler B J, Hoffman G S. Open label trial of tamoxifen in schleroderma. Clin Exp Rheumatol 2003; 21:99-102.
26. Feghali C A, Wright T M. Identification of multiple, deferentially expressed messenger RNAs in dermal fibroblasts from patients with systemic sclerosis. Arthritis Rheum 1999; 42:1451-57.
27. Redaelli C, Granucci F, De Gioia L, Cipolla L. Synthesis and biological activity of Akt/PI3K inhibitors. Mini Rev med Chem 2006; 6:1127-36.
28. Ashcroft G S, Dodsworth J, van Boxtel E, Tarnuzzer R W, Horan M A, Schultz G S, Ferguson M W. Estrogen accelerates cutaneous wound healing associated with an increase in TGF-beta1 levels. Nat Med 1997; 3:1209-15.

29. Ashcroft G S, Greenwell-wild T, Horan M A, Wahl S M, Ferguson M W. Topical estrogen accelerates cutaneous wound healing in aged humans associated with an altered inflammation response. Am J Path 1999; 155:1137-46.
30. Mercier I, Colombo F, Mader S, Calderone A. Ovarian hormones induce TGF-beta (3) and fibronectin mRNAs but exhibit a disparate action on cardiac fibroblast proliferation. Cardiovasc Res 2002; 53:728-39.
31. Meyringer R, Neumann E, Judex M, Landthaler M, Kullmann F, Scholmerich J, Gay S, Tamer I H, Distler O, Muller-Ladner U. Analysis of gene expression patterns in systemic sclerosis fibroblasts using RNA arbitrarily primed-polymerase chain reaction for different display. J Rheumatol 2007; 34:747-53.
32. Ziegler W F, Bernstein I, Badger G, Leavitt T, Cerrero M L. Regional hemodinamic adaptation during the menstrual cycle. Obstet Gynecol 1999; 94:695-99.
33. Bakos O, Lundkvist O, Wide L, Bergh T. Ultrasonographical and hormonal description of ovulatory menstrual cycle. Acta Obstet Gynecol Scand 1994; 73:790-96.
34. Notelovitz M, Funk S, Nanavati N, Mazzeo M. Estradiol absorption from vaginal tablets in postmenoposal women. Obstet Gynecol 2002; 99:556-62.
35. Pilewski J M, Liu L, Henry A C, Knauer A V, Feghali-Bostwick C A. Insulin-like growth factor binding protein 3 and 5 are overexpressed in idiopathic pulmonary fibrosis and contribute to extracellular matrix deposition. Am J Pathol 2005; 166:399-407.
36. Henderson B E, Feigelson H S. Hormonal carcinogenesis. Carcinogenesis 2000; 21:427-33.
37. Harris H A, Albert L M, Leathurby Y, Malamas M S, Mewshaw R E, Miller C P, Kharode Y P, Marzolf J, Komm B S, Winneker R C, Frail D E, Henderson R A, Zhu Y, Keith J C Jr. Evaluation of an estrogen receptor-beta agonist in animal models of human disease. Endocrinology 2003; 144:4241-49.
38. Wise P M, Dubai D B, Wilson M E, Rau S W, Bottner M. Minireview.Neuroprotective effects of estrogen: new insights into mechanisms of action. Endocrinology 2001; 142:969-73.
39. Hum P D, Sacco R L. Sex, steroids and stroke: introduction. Stroke 2004; 35:2642-43.
40. Ohlsson C, Hellberg N, Parini P, Vidal O, Bohlooly-Y M, Rudling M, Lindberg M K, Warner M, Angelin B Gustafsson J A. Obesity and disturbed lipoprotein profile in estrogen receptor-alpha-deficient male mice. Biochem Biophys Res Commun 2006; 278:640-45.
41. Lloyd, D O, Meegan, M J. Recent advances in estrogen receptor antagonists. IDrugs 2000; 3(6):632-642.
42. Geiser, A G et al., A new selective estrogen receptor modulator with potent uterine antagonist activity, agonist activity in bone, and minimal ovarian stimulation. Endocrinol. 2005; 146(10):4524-4535.
43. Bowers, J L et al., Resveratrol acts as a mixed agonist/antagonist for estrogen receptors α and β. 2000; 141(10): 3657-3667.
44. Rich R L and Myszka, D G. Resolving estrogen receptor agonist/antagonist kinetics using Biacore's SPR technology. Biacore J. 2002; 2:4-6.
45. Zwart, W. et al., Classification of anti-estrogens according to intramolecular FRET effects on phospho-mutants of ERα. Mol. Cancer Ther. 2007; 6:1526-1633.
46. Diel P, Schmidt S, Vollmer G. In vivo test systems for the quantitative and qualitative analysis of the biological activity of phytoestrogens. J. Chrom. B. Analyt. Technol. Biomed. Life Sci. 2002; 777(1-2): 191-202.
47. Odum J. et al., The rodent uterotrophic assay: critical protocol features, studies with nonyl phenols, and comparison with a yeast estrogenicity assay. Regul. Toxicol. Pharmacol. 1997; 25(2):176-188.
48. Liu, J. et al., A homogeneous in vitro functional assay for estrogen receptors: coactivator recruitment. Mol. Endocrinol. 2003; 17(3):346-355.
49. Melamed, M. et al., Molecular and kinetic basis for the mixed agonist/antagonist activity of estriol. Molecular Endocrinol. 1997; 11:1868-1878.
50. Meiyun, F. et al., Characterization of molecular and structural determinants of selective estrogen receptor down-regulators. Breast Cancer Res Treatment 1007; 103(1):37-44.
51. Tremblay, A. et al., EM-800, a novel antiestrogen, acts as a pure antagonist of the transcriptional functions of estrogen receptors alpha and beta. Endocrinol. 1998; 139(1): 111-118.
52. Blizzard, T A, et al., Estrogen receptor ligands. Part 13: Dihydrobenzoxathiin SERAMs with an optimized antagonist side chain. Bioorg. Med. Chem. Lett. 2005; 15(17): 3912-3916.
53. Cvoro, A. et al., Selective estrogen receptor-3 agonists repress transcription of proinflammatory genes. J Immunol. 2008; 180:630-636.
54. Harris, H A et al., A selective estrogen receptor-β agonist causes lesion regression in an experimentally induced model of endometriosis. Human Reprod. 2005; 20(4) 936-941.
55. Schrepfer, S. et al., The selective estrogen receptor-beta agonist biochanin A shows vasculoprotective effects without uterotrophic activity. Menopause. 2006; 13(3):489-499.
56. Curran, M., Wiseman, L. Drugs 2001; 61(6):807-813.
57. Gibson T. and Grhame, R. Cyclofenil treatment of scleroderma—a controlled study. Br. J. Rheumatol. 22(4):218-223.
58. Yasuoka H. et al., Human skin culture as an ex vivo model for assessing the fibrotic effects of insulin-like growth factor binding proteins. Open J. Rheumatol. 2008; 2:17-22. E published Mar. 28, 2008.
59. Hall, G., Phillips, T J. Estrogen and the skin: the effects of estrogen, menopause, and hormone replacement therapy on the skin. J. Am. Acad. Dermatol. 2005; 53:555-568.
60. Brincat, M., Moniz, C. J., Studd, J. W., Darby, A., Magos, A., Emburey, G., Versi, E. Long-term effects of the menopause and sex hormones on skin thickness. Br J Obstet Gynaecol. 1985 March; 92(3):256-9.
61. Maheux, R., Naud, F., Rioux, M., Grenier, R., Lemay, A., Guy, J., Langevin M. A randomized, double-blind, placebo-controlled study on the effect of conjugated estrogens on skin thickness. Am J Obstet Gynecol. 1994 February; 170(2):642-9.
62. Callens, A., Vaillant, L., Lecompte, P. et al. Does hormonal skin aging exist? A study of the influence of different hormone therapy regimens on the skin of post-menopausal women using non-invasive measurement techniques. Dermatol. 1996, 193:289-94.
63. Sun, J., Huang, Y. R., Harrington, W. R., Sheng, S., Katzenellenbogen, J. A., Katzenellenbogen, B. S. Antagonists selective for estrogen receptor alpha. Endocrinol. 2002. 143(3):941-947.
64. Soldano, S., Montagna, P., Brizzolara, R., Sulli, A., Parodi, A., Seriolo, B., Paolino, S., Villaggio, B., Cutolo, M. Effects of estrogens on extracellular matrix synthesis in cultures of human normal and scleroderma skin fibroblasts. Ann. N.Y. Acad. Sci. 2010. 1193:25-29.

Various references are cited herein, the contents of which are hereby incorporated by reference in their entireties.

We claim:

1. A method for treating a scleroderma comprising administering, to a subject in need of such treatment, an effective amount of an estrogen receptor antagonist, wherein the estrogen receptor antagonist is selected from the group consisting of fulvestrant, GW7604, EM-800, and compound 35 of FIG. 10G.

2. The method of claim 1, further comprising administering an effective amount of an estrogen receptor beta agonist.

3. The method of claim 1, further comprising administering an effective amount of a compound that inhibits estrogen synthesis.

* * * * *